(12) United States Patent
Tandon et al.

(10) Patent No.: US 6,998,469 B2
(45) Date of Patent: Feb. 14, 2006

(54) PLATELET MEMBRANE GLYCOPROTEIN VI (GPVI) DNA AND PROTEIN SEQUENCES, AND USES THEREOF

(75) Inventors: Narendra Nath Tandon, Gaithersburg, MD (US); Bing Sun, North Potomac, MD (US); Takashi Nakamura, Hyogo (JP); Naomasa Yamamoto, Gaithersburg, MD (US)

(73) Assignee: Otsuka America Pharmaceutical, Inc., Rockville, MD (US)

(*) Notice: Subject to any disclaimer, the term of this patent is extended or adjusted under 35 U.S.C. 154(b) by 241 days.

(21) Appl. No.: 10/446,826

(22) Filed: May 29, 2003

(65) Prior Publication Data

US 2004/0152628 A9    Aug. 5, 2004

Related U.S. Application Data

(63) Continuation of application No. 09/653,255, filed on Aug. 31, 2000, now abandoned.

(60) Provisional application No. 60/152,197, filed on Sep. 1, 1999, provisional application No. 60/158,251, filed on Oct. 8, 1999.

(51) Int. Cl.
C07K 16/34    (2006.01)
(52) U.S. Cl. ............................... 530/388.25; 530/389.3
(58) Field of Classification Search .......... 530/388.25, 530/389.3
See application file for complete search history.

(56) References Cited

FOREIGN PATENT DOCUMENTS

WO    WO 01/00810    1/2001

OTHER PUBLICATIONS

Qian et al., 2002, *Human Antibodies* 11:97-105.

*Primary Examiner*—Christina Chan
*Assistant Examiner*—Maher Haddad
(74) *Attorney, Agent, or Firm*—Finnegan, Henderson, Farabow, Garrett & Dunner, LLP

(57) ABSTRACT

The present invention comprises a method of purifying GPVI, GPVI peptides, cDNA and protein sequence, and methods for using GPVI and antibodies directed against GPVI.

3 Claims, 13 Drawing Sheets

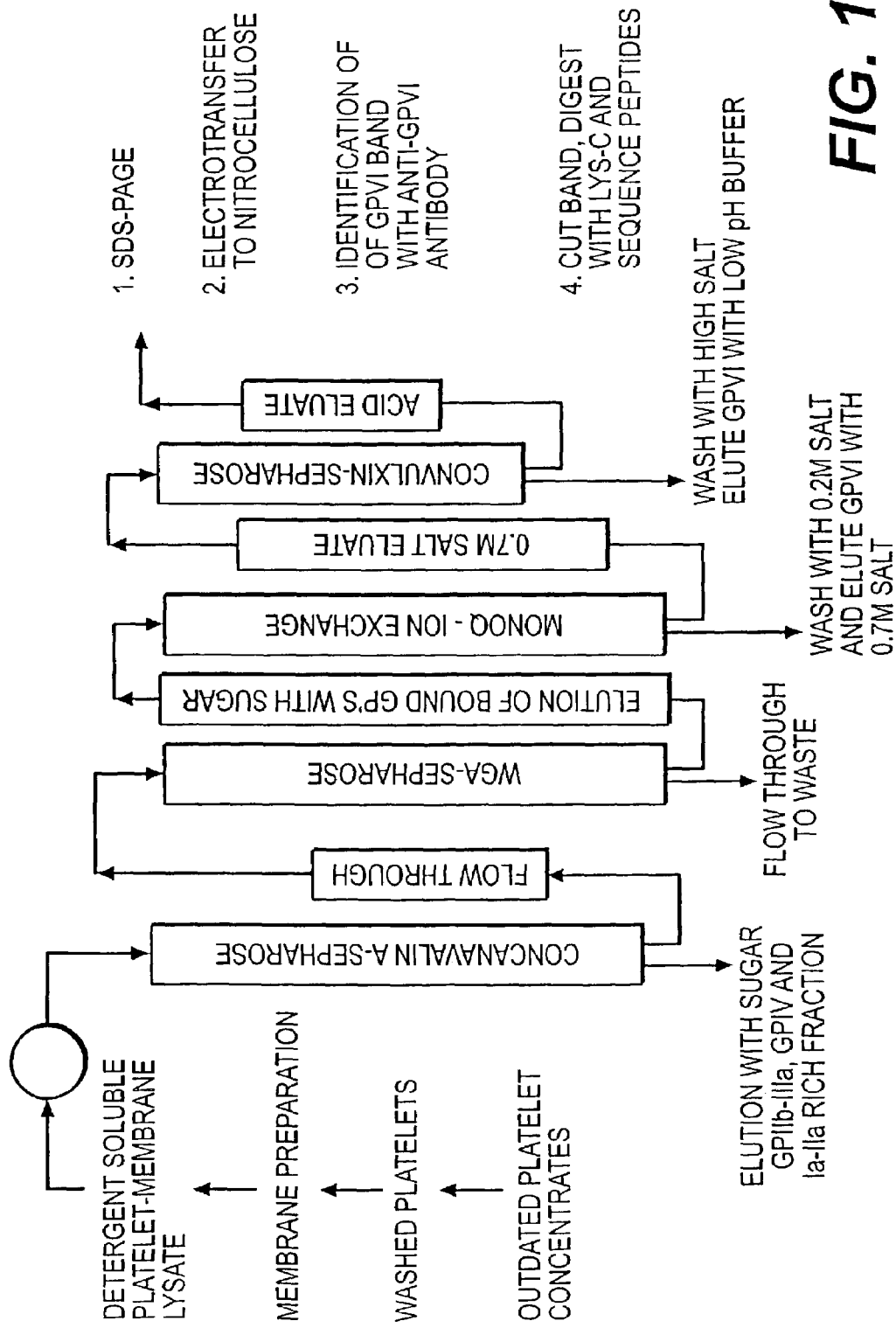

Partial cDNA Nucleotide Sequence Encoding GPVI

SEQ ID NO: 1

ACAGGGCTGA GGAACCATGT CTCCATCCCC GACCGCCCTC TTCTGTCTTG
TGTCCCGACT CCTTGGTACA GAGGTAGGGG CTGGCGGGAG AAGACAGAAC

GGCTGTGTCY GGGGCGTGTG CCAGCGCAGA GTGGACCGCT CCCCAAGCCC
CCGACACAGR CCCCGCACAC GGTCGCGTCT CACCTGGCGA GGGGTTCGGG

TCCCTCCAGG CTCTGCCCAG CTCCCTGGTG CCCCTGGAGA AGCCAGTGAC
AGGGAGGTCC GAGACGGGTC GAGGGACCAC GGGGACCTCT TCGGTCACTG

CCTCCGGTGC CAGGGACCTC CGGGCGTGGA CCTGTACCGC CTGGAGAAGC
GGAGGCCACG GTCCCTGGAG GCCCGCACCT GGACATGGCG GACCTCTTCG

TGAGTTCCAG CAGGTACCAC GATCAGGCCG TCCTCTTCAT
ACTCAAGGTC GTCCATGGTG CTAGTCCGGC AGGAGAAGTA

GPVI Peptide Sequences encoded by the Isolated cDNA Fragment

SEQ ID NO: 2

MSPSPTALFC LGLCLGRVPA QSGPLPKPSL QALPSSLVPL
EKPVTLRCQG PPGVDLYRLE KLSSSRYHDQ AVLF

SEQ ID NO: 3

MSPSPTALFC LGLCPGRVPA QSGPLPKPSL QALPSSLVPL
EKPVTLRCQG PPGVDLYRLE KLSSSRYHDQ AVLF

*FIG. 2*

GPVI Full-Length cDNA Sequence

SEQ ID NO: 4

ACAGGGCTGA GGAACCATGT CTCCATCCCC GACCGCCCTC TTCTGTCTTG
TGTCCCGACT CCTTGGTACA GAGGTAGGGG CTGGCGGGAG AAGACAGAAC

GGCTGTGTCT GGGGCGTGTG CCAGCGCAGA GTGGACCGCT CCCCAAGCCC
CCGACACAGA CCCCGCACAC GGTCGCGTCT CACCTGGCGA GGGGTTCGGG

TCCCTCCAGG CTCTGCCCAG CTCCCTGGTG CCCCTGGAGA AGCCAGTGAC
AGGGAGGTCC GAGACGGGTC GAGGGACCAC GGGGACCTCT TCGGTCACTG

CCTCCGGTGC CAGGGACCTC CGGGCGTGGA CCTGTACCGC CTGGAGAAGC
GGAGGCCACG GTCCCTGGAG CCCGCACCT GGACATGGCG ACCTCTTCG

TGAGTTCCAG CAGGTACCAG GATCAGGCAG TCCTCTTCAT CCCGGCCATG
ACTCAAGGTC GTCCATGGTC CTAGTCCGTC AGGAGAAGTA GGGCCGGTAC

AAGAGAAGTC TGGCTGGACG CTACCGCTGC TCCTACCAGA ACGGAAGCCT
TTCTCTTCAG ACCGACCTGC GATGGCGACG AGGATGGTCT TGCCTTCGGA

CTGGTCCCTG CCCAACGACC AGCTGGAGCT CGTTGCCACG GGAGTTTTTG
GACCAGGGAC GGGTTGCTGG TCGACCTCGA GCAACGGTGC CCTCAAAAAC

CCAAACCCTC GCTCTCAGCC CAGCCCGGCC CGGCGGTGTC GTCAGGAGGG
GGTTTGGGAG CGAGAGTCGG GTCGGGCCGG CCGCCACAG CAGTCCTCCC

GACGTAACCC TACAGTGTCA GACTCGGTAT GGCTTTGACC AATTTGCTCT
CTGCATTGGG ATGTCACAGT CTGAGCCATA CCGAAACTGG TTAAACGAGA

GTACAAGGAA GGGGACCCTG CGCCCTACAA GAATCCCGAG AGATGGTACC
CATGTTCCTT CCCCTGGGAC GCGGGATGTT CTTAGGGCTC TCTACCATGG

GGGCTAGTTT CCCCATCATC ACGGTGACCG CCGCCCACAG CGGAACCTAC
CCCGATCAAA GGGGTAGTAG TGCCACTGGC GGCGGGTGTC GCCTTGGATG

CGATGCTACA GCTTCTCCAG CAGGGACCCA TACCTGTGGT CGGCCCCCAG
GCTACGATGT CGAAGAGGTC GTCCCTGGGT ATGGACACCA GCCGGGGGTC

CGACCCCCTG GAGCTTGTGG TCACAGGAAC CTCTGTGACC CCCAGCCGGT
GCTGGGGGAC CTCGAACACC AGTGTCCTTG AGACACTGG GGGTCGGCCA

*FIG. 3A*

```
TACCAACAGA ACCACCTTCC TCGGTAGCAG AATTCTCAGA AGCCACCGCT
ATGGTTGTCT TGGTGGAAGG AGCCATCGTC TTAAGAGTCT TCGGTGGCGA

GAACTGACCG TCTCATTCAC AAACAAAGTC TTCACAACTG AGACTTCTAG
CTTGACTGGC AGAGTAAGTG TTTGTTTCAG AAGTGTTGAC TCTGAAGATC

GAGTATCACC ACCAGTCCAA AGGAGTCAGA CTCTCCAGCT GGTCCTGCCC
CTCATAGTGG TGGTCAGGTT TCCTCAGTCT GAGAGGTCGA CCAGGACGGG

GCCAGTACTA CACCAAGGGC AACCTGGTCC GGATATGCCT CGGGGCTGTG
CGGTCATGAT GTGGTTCCCG TTGGACCAGG CCTATACGGA GCCCCGACAC

ATCCTAATAA TCCTGGCGGG GTTTCTGGCA GAGGACTGGC ACAGCCGGAG
TAGGATTATT AGGACCGCCC CAAAGACCGT CTCCTGACCG TGTCGGCCTC

GAAGCGCCTG CGGCACAGGG GCAGGGCTGT GCAGAGGCCG CTTCCGCCCC
CTTCGCGGAC GCCGTGTCCC CGTCCCGACA CGTCTCCGGC GAAGGCGGGG

TGCCGCCCCT CCCGCAGACC CGGAAATCAC ACGGGGGTCA GGATGGAGGC
ACGGCGGGGA GGGCGTCTGG GCCTTTAGTG TGCCCCCAGT CCTACCTCCG

CGACAGGATG TTCACAGCCG CGGGTTATGT TCATGACCGC TGAACCCCAG
GCTGTCCTAC AAGTGTCGGC GCCCAATACA AGTACTGGCG ACTTGGGGTC

GCACGGTCGT ATCCAAGGGA GGGATCATGG CATGGGAGGC GACTCAAAGA
CGTGCCAGCA TAGGTTCCCT CCCTAGTACC GTACCCTCCG CTGAGTTTCT

CTGGCGTGTG TGGAGCGTGG AAGCAGGAGG GCAGAGGCTA CAGCTGTGGA
GACCGCACAC ACCTCGCACC TTCGTCCTCC CGTCTCCGAT GTCGACACCT

AACGAGGCCA TGCTGCCTCC TCCTGGTGTT CCATCAGGGA TCCGTCGGCC
TTGCTCCGGT ACGACGGAGG AGGACCACAA GGTAGTCCCT AGGCAGCCGG

AGTGTCTGTC TGTCTGTCTG CCTCTCTGTC TGAGGGCACC CTCCATTTGG
TCACAGACAG ACAGACAGAC GGAGAGACAG ACTCCCGTGG GAGGTAAACC

GATGGAAGGA ATCTGTGGAG ACCCCATCCT CCTCCCTGCA CACTGTGGAT
CTACCTTCCT TAGACACCTC TGGGGTAGGA GGAGGGACGT GTGACACCTA

GACATGGTAC CCTGGCTGGA CCACATACTG GCCTCTTTCT TCAACCTCTC
CTGTACCATG GGACCGACCT GGTGTATGAC CGGAGAAAGA AGTTGGAGAG

TAATATGGGC TCCAGACGGA TCTCTAAGGT TCCCAGCTCT CAGGGTTGAC
ATTATACCCG AGGTCTGCCT AGAGATTCCA AGGGTCGAGA GTCCCAACTG
```

*FIG. 3B*

```
TCTGTTCCAT CCTCTGTGCA AAATCCTCCT GTGCTTCCCT TTGGCCCTCT
AGACAAGGTA GGAGACACGT TTTAGGAGGA CACGAAGGGA AACCGGGAGA

GTGCTCTTGT CTGGTTTTCC CCAGAAACTC TCACCCTCAC TCCATCTCCC
CACGAGAACA GACCAAAAGG GGTCTTTGAG AGTGGGAGTG AGGTAGAGGG

ACTGCAGTCT AACAAATCTC CTTTCGTCTC TCAGAACGGG TCTTGCAGGC
TGACGTCAGA TTGTTTAGAG GAAAGCAGAG AGTCTTGCCC AGAACGTCCG

AGTTTGGGTA TGTCATTCAT TTTCCTTAGT GTAAAACTAG CACGTTGCCC
TCAAACCCAT ACAGTAAGTA AAAGGAATCA CATTTTGATC GTGCAACGGG

GCTTCCCTTC ACATTAGAAA ACAAGATCAG CCTGTGCAAC ATGGTGAAAC
CGAAGGGAAG TGTAATCTTT TGTTCTAGTC GGACACGTTG TACCACTTTG

CTCATCTCTA CCAACAAAAA AAAAAAAAA A
GAGTAGAGAT GGTTGTTTTT TTTTTTTTT T
```

GPVI Peptide Sequence Encoded by the Isolated Full-Length cDNA

SEQ ID NO:5

```
MSPSPTALFC LGLCLGRVPA QSGPLPKPSL QALPSSLVPL EKPVTLRCQG
PPGVDLYRLE KLSSSRYQDQ AVLEIPAMKR SLAGRYRCSY QNGSLWSLPS
DQLELVATGV FAKBSLSAQP GPAVSSGGDV TLQCQTRYGF DQFALYKEGD
PAPYKNPERW YRASFBIITV TAAHSGTYRC YSFSSRDPYL WSAPSDPLEL
VVTGTSVTPS RLPTEPPSSV AEFSEATAEL TVSFTNKVFT TETSRSITTS
PKESDSPAGP ARQYYTKGNL VRICLGAVIL IILAGFLAED WHSRRKRLRH
RGRAVQRPLP PLPPLPQTRK SHGGQDGGRQ DVHSRGLCS
```

FIG. 3C

```
       - (SEQ ID NO:36)
 901 - CAACTTGAGAAGATCAAAAAACAACTAATTATTCGAAACGATGAGATTTCCTTCAATTTT - 960
       -                                    (SEQ ID NO:37) M  R  F  P  S  I  F
 961 - TACTGCTGTTTTATTCGCAGCATCCTCCGCATTAGCTGCTCCAGTCAACACTACAACAGA - 1020
       - T  A  V  L  F  A  A  S  S  A  L  A  A  P  V  N  T  T  T  E
1021 - AGATGAAACGGCACAAATTCCGGCTGAAGCTGTCATCGGTTACTCAGATTTAGAAGGGGA - 1080
       - D  E  T  A  Q  I  P  A  E  A  V  I  G  Y  S  D  L  E  G  D
1081 - TTTCGATGTTGCTGTTTTGCCATTTTCCAACAGCACAAATAACGGGTTATTGTTTATAAA - 1140
       - F  D  V  A  V  L  P  F  S  N  S  T  N  N  G  L  L  F  I  N
1141 - TACTACTATTGCCAGCATTGCTGCTAAAGAAGAAGGGGTATCTCTCGAGAAAAGAGAGGC - 1200
       - T  T  I  A  S  I  A  A  K  E  E  G  V  S  L  E  K  R  E  A
1201 - TGAAGCTGAATTCACGTGGCCCAGCCGGCCTCAGAGTGGACCGCTCCCCAAGCCCTCCCT - 1260
       - E  A  E  F  T  W  P  S  R  P  Q  S  G  P  L  P  K  P  S  L
1261 - CCAGGCTCTGCCCAGCTCCCTGGTGCCCCTGGAGAAGCCAGTGACCCTCCGGTGCCAGGG - 1320
       - Q  A  L  P  S  S  L  V  P  L  E  K  P  V  T  L  R  C  Q  G
1321 - ACCTCCGGGCGTGGACCTGTACCGCCTGGAGAAGCTGAGTTCCAGCAGGTACCAGGATCA - 1380
       - P  P  G  V  D  L  Y  R  L  E  K  L  S  S  S  R  Y  Q  D  Q
1381 - GGCAGTCCTCTTCATCCCGGCCATGAAGAGAAGTCTGGCTGGACGCTACCGCTGCTCCTA - 1440
       - A  V  L  F  I  P  A  M  K  R  S  L  A  G  R  Y  R  C  S  Y
1441 - CCAGAACGGAAGCCTCTGGTCCCTGCCCAGCGACCAGCTGGAGCTCGTTGCCACGGGAGT - 1500
       - Q  N  G  S  L  W  S  L  P  S  D  Q  L  E  L  V  A  T  G  V
1501 - TTTTGCCAAACCCTCGCTCTCAGCCCAGCCCGGCCCGGCGGTGTCGTCAGGAGGGGACGT - 1560
       - F  A  K  P  S  L  S  A  Q  P  G  P  A  V  S  S  G  G  D  V
1561 - AACCCTACAGTGTCAGACTCGGTATGGCTTTGACCAATTTGCTCTGTACAAGGAAGGGGA - 1620
       - T  L  Q  C  Q  T  R  Y  G  F  D  Q  F  A  L  Y  K  E  G  D
1621 - CCCTGCGCCCTACAAGAATCCCGAGAGATGGTACCGGGCTAGTTTCCCCATCATCACGGT - 1680
       - P  A  P  Y  K  N  P  E  R  W  Y  R  A  S  F  P  I  I  T  V
1681 - GACCGCCGCCCACAGCGGAACCTACCGATGCTACAGCTTCTCCAGCAGGGACCCATACCT - 1740
       - T  A  A  H  S  G  T  Y  R  C  Y  S  F  S  S  R  D  P  Y  L
1741 - GTGGTCGGCCCCCAGCGACCCCCTGGAGCTTGTGGTCACAGGAACCTCTGTGACCCCCAG - 1800
       - W  S  A  P  S  D  P  L  E  L  V  V  T  G  T  S  V  T  P  S
1801 - CCGGTTACCAACAGAACCACCTTCCTCGGTAGCAGAATTCTCAGAAGCCACCGCTGAACT - 1860
       - R  L  P  T  E  P  P  S  S  V  A  E  F  S  E  A  T  A  E  L
1861 - GACCGTCTCATTCACAAACAAAGTCTTCACAACTGAGACTTCTAGGAGTATCACCACCAG - 1920
       - T  V  S  F  T  N  K  V  F  T  T  E  T  S  R  S  I  T  T  S
1921 - TCCAAAGGAGTCAGACTCTCCAGCTGGTCCTGCCCGCCAGTACTACACCAAGGGCAACGG - 1980
       - P  K  E  S  D  S  P  A  G  P  A  R  Q  Y  Y  T  K  G  N  G
1981 - TCTAGAACAAAAACTCATCTCAGAAGAGGATCTGAATAGCGCCGTCGACCATCATCATCA - 2040
       - L  E  Q  K  L  I  S  E  E  D  L  N  S  A  V  D  H  H  H  H
2041 - TCATCATTGAGTTTGTAGCCTTAGACATGACTGTTCCTCAGTTCAAGTTGGGCACTTACG - 2100
       - H  H  *
```

FIG. 5

PLATELET MEMBRANE GLYCOPROTEIN VI (GPVI) DNA AND PROTEIN SEQUENCES, AND USES THEREOF

CROSS REFERENCE TO RELATED APPLICATIONS

This application is a continuation of Ser. No. 09/653,255, filed Aug. 31, 2000 and now abandoned, which claims priority under 35 U.S.C. §119 of U.S. provisional applications Ser. No. 60/152,197, filed Sep. 1, 1999, and Ser. No. 60/158,251, filed Oct. 8, 1999, both of which are specifically incorporated by reference.

FIELD OF THE INVENTION

The present invention relates to polypeptides and cDNA sequences of Platelet Membrane Glycoprotein VI (GPVI) and variants thereof, antibodies generated against these polypeptides, and to the use of these polypeptides, polynucleotide sequences, and antibodies as research and immunotherapeutic agents, in particular, as therapeutic agents for treating thrombosis and other vascular diseases.

BACKGROUND

Platelets are small, anuclear blood cells which are essential to hemostatic control and wound healing. Circulating platelets are fairly quiescent under normal conditions. However, when a blood vessel is torn or damaged, platelets are exposed to various factors that instigate complicated and interconnected cellular programs leading to blood coagulation and clot formation, which are reviewed in *Mechanisms of Platelet Activation and Control*, K. S. Authi, S. P. Watson, and V. V. Kakar (eds.) Plenum Press, 1993 (incorporated herein by reference). The activation of these cellular programs result in dramatic increases in membrane adhesive properties, platelet aggregation, and the release of vasoconstrictive and fibrinolytic factors. As a consequence, a clot forms at the site of trauma, plugging any breach in the vessel wall and providing a substrate for fibroblast invasion and repair.

The early events in the clotting process can be functionally separated into two primary components: adhesion and activation. Adhesion is the process of "sticking" platelets to the injured vascular wall, whereas activation initiates complex physiological changes inside the cell. Together, these two processes result in platelet agglutination and, ultimately, in the production of a mature clot.

Most steps in these processes depend on the interaction of extracellular ligands with specific receptors embedded in the platelet cell membrane. In vivo, the first visible change in platelet behavior is the adhesion of platelets to an area of denuded endothelium. The initial contact involves interaction of the platelet glycoprotein complex GPIb-V-IX with von Willebrand factor (vWf) bound to the exposed epithelium. This interaction appears to be a reversible process which results in the "rolling" of platelets along the vessel wall. Although the vWf interaction does not completely immobilize circulating platelets, it is essential to platelet adherence under high blood flow conditions. Subsequent irreversible binding of glycoprotein GPIa-IIa (also known as integrin $\alpha_2\beta_1$) to endothelial collagen stabilizes the vWf interaction event, firmly anchoring the platelet to the vessel wall. Unlike vWf, collagen adhesion appears to be a slower process and is effective only under low flow conditions, or after platelets have been partially arrested by vWf interactions. In addition, GPIa-IIa binding induces the flattening (spreading) of platelet against the vessel wall. Spreading promotes the binding of other subendothelial adhesion factors including fibronectin, vitronectin and thrombospondin. These post-spreading interactions further stabilize the adhesion of platelets to the vessel wall.

GPIa-IIa-dependent spreading represents one of the earliest manifestations of the activation process. Stimulation of GPIa-IIa and other collagen receptors induces a host of physiological changes. Among these are altered cell surface adhesion properties that result in platelet-platelet aggregation, and the secretion of various bioactive compounds. These compounds include the vasoconstrictor, epinephrine, and proclotting factors, which activate thrombin and lead to polymerization of fibrinogen into the fibrin threads of a mature clot. In addition, activated platelets release ADP and thromboxane $A_2$ (TXA2). These powerful thrombogenic factors amplify the initial activation signal, recruiting additional platelets into the activated state.

In addition to GPIa-IIa, at least two other collagen receptors are expressed on the platelet cell surface, namely, GPIV (CD36), and GPVI. Recent evidence suggests that both of these receptors contribute to platelet activation. Nevertheless, roughly 3 to 10% of the Japanese population lack GPIV and these individuals do not appear to have any hemostatic abnormality. In fact, it has been speculated that these individuals may be protected against thrombotic ailments. In contrast, the substantially more rare individuals lacking either GPIa-IIa or GPVI exhibit prolonged bleeding times. GPIa-IIa deficiencies generally lead to more severe bleeding disorders than those of GPVI etiology. Nevertheless, these patients rarely present the life threatening hemophilias such as that seen in individuals lacking von Willibrand factor.

Observations of human variants, along with recent in vitro data, suggest that the three collagen receptors act in concert to mediate collagen-platelet interactions. In vitro, for instance, it is now possible to block the activity of each collagen receptor with antibodies specific for the collagen receptor sites. Individually, each antibody partially inhibits platelet adhesion to collagen and pairwise combinations of antibodies are significantly more inhibitory, particularly when GPIa-IIa and GPVI are inhibited simultaneously. Moreover, these studies demonstrate that GPIV, GPIa-IIa, and GPVI contribute to thrombosis through two distinct pathways, mechanistically distinguishable by the requirement for divalent metal cations.

Biochemical and sequence information indicates that GIPIa-IIa is a cation-dependent integrin-type receptor. In contrast, biochemical studies reveal that GPIV and GPVI do not require divalent metal cations and are thus non-integrin type. Of the non-integrin class, observations of human subjects clearly suggest that GPVI is more important than GPIV in the primary adhesion process. Indeed, in vitro experiments where GPIa-IIa function is blocked by chelating divalant cations, antibodies directed against GPVI completely abolish collagen-platelet interaction.

GPVI was first identified about 30 years ago by isoelectric focusing and electrophoresis. Until recently, its function was completely undefined and it was known merely as a platelet glycoprotein with a molecular mass of approximately 62 kDa under reducing condition. However, beginning around 1987, Dr. Minoru Okuma and associates examined several patients with a form of thrombocytopenic purpura, a bleeding/bruising syndrome characterized by accelerated platelet destruction and decreased numbers of circulating platelets. The platelets in some of Dr. Okuma's patients aggregated normally in response to most agonists, including ADP, thrombin, Ristocetin, and calcium ionophore (A23187) but were markedly unresponsive to collagen. Moreover, these platelets were found to have reduced amounts, or even totally lack, the 62 kDa glycoprotein. Sugiyama et al., Blood 69:1712–20 (1987); Moroi et al., J. Clin. Invest. 84:1440–45 (1989); Ryo et al., Am. J. Hematol. 39:25–31 (1992); and Arai et al., Brit. J. Haematol. 89:124–130 (1995).

The key reagent in the early studies of GPVI function came from the one of Dr. Okuma's thrombocytopenic purpura patients. This patient presented with massive, unexplained bleeding and was treated by transfusion with HLA-matched platelets. Subsequent detailed examination of the patient's blood revealed a total lack of GPVI. Most surprisingly, because this patient totally lacked GPVI, her immune system had identified the GPVI molecules on the transfused platelets as foreign antigens and produced polyclonal antibodies against GPVI. Sugiyama et al., Blood 69:1712–20 (1987).

A naturally occurring antibody is composed of two identical binding sites, specific for a single antigenic epitope. The two antigen-specific portions are linked by a common stem, or Fc domain, to form a complex capable of binding to two identical antigen molecules. Moreover, the divalent nature of the antibody, in conjunction with aggregatory properties of the Fc domain, allow cross-linking and aggregation of many specific antigen molecules. Dr. Okuma found that the divalent antibodies from the patient's serum caused a massive aggregation response when mixed with normal platelets. Conversely, when the antigen-specific domains are rendered monovalent by enzymatic removal of linking Fc domain, the resulting Fab fragments completely abolished collagen-induced aggregation of normal platelets and inhibited platelet-collagen adhesion.

Dr. Okuma has graciously made this rare serum available to the scientific community. Unfortunately, the supply is limited, and the circumstances surrounding its discovery are virtually irreproducible. Although the Okuma serum made possible much of the research into the function of GPVI, and had long provided the sole method of identifying a protein as GPVI, it has recently been discovered that the lectin, convulixin, specifically binds to GPVI with high affinity and can can be labeled as probe to identify the GPVI protein. (Francishetti et al., Toxicon 35:1217–28 (1997); Polgar et al., J. Biol. Chem. 272(24):13576–83 (1997); and Jandrot-Perrus et al., J. Biol. Chem. 272(2):27035–41 (1997) (which are both incorporated herein by reference.) Convulxin is a venom component from the tropical rattlesnake *Crotalus durissus terrificus*. In its native, divalent form, convuixin is a potent inducer of platelet aggregation and secretion of proaggregatory and proclotting factors. The divalent nature of convulxin is critical to the aggregatory effect. Although the underlying physiology of the reaction is unclear, individual convulxin subunits still bind to GPVI, but inhibits, rather than induces aggregation. It has been suggested that monovalent convuixin blocks the transmission of collagen-induced signals to the interior of the cell.

Recent evidence suggests that GPVI may be associated in the cell membrane with Fc receptor y (FcyRIIa). It is currently believed that collagen binding to GPVI induces tyrosine phosphorylation of FcyRII. Phosphorylated FcyRII then activates the Syk kinase, ultimately leading to a cascade of intracellular events including phospho-activation of cSrc, protein kinase c, and phospholipase C-γ2. These events ultimately result in increased intercellular calcium levels and the secretion of proaggregatory and proclotting factors.

It is now accepted that GPVI is the principle receptor for collagen-induced platelet activation, and is a critical conduit for signal transduction. Ichinohe et al., J. Biol Chem. 270 (47):28029–28036 (1995); Tsuji et al., J. Biol Chem. 272 (28):23528–31 (1997). In contrast, the other major collagen receptor in platelets, GPIa-IIa, is primarily involved with the cation-dependent processes of spreading and cell-cell cohesion.

Yet, despite the availability of research tools to elucidate the general mechanisms of GPVI function, this protein has proven remarkably refractory to purification. As a consequence, it has been impossible to generate anti-GPVI antibodies by conventional means, or even to purify sufficient protein to obtain a partial amino acid sequence. Lacking these reagents, no one has been able to identify the GPVI nucleotide or protein sequence. Indeed, Dr. Okuma, himself, has been unable to obtain the GPVI sequence. The lack of sequence data has thus severely hampered structure-function studies limited the search for GPVI agonists and antagonists.

The need in the art for GPVI sequence information, and GPVI antagonists, in particular, is highlighted by the unfortunate fact that inappropriate platelet aggregation and clot formation is a major etiologic factor in a wide range of human diseases, most commonly, vascular diseases. Excessive platelet aggregation in arteries and veins contributes to atherosclerotic and arteriosclerotic plaques which reduce the flow of blood to sensitive tissues. Ultimately, this platelet-dependent buildup may manifest as acute myocardial infarct, chronic unstable angina, transient ischemia, stroke, peripheral vascular disease, arterial thrombosis, preeclampsia, pulmonary embolism, restenois, and various other conditions.

These conditions typically begin with an abnormal clot that develops in a blood vessel, called a thrombus. Once a clot has developed, continued flow of blood past the clot is likely to break it free from its attachment. Such freely flowing clots are known as emboli. Emboli generally travel through the circulation until trapped in a narrow point in the circulatory system. This occlusion may occur in the brain, lung or cornary arteries, resulting in pain, disability or death.

Intravascular clots may result from naturally-occuring sclerosis, septicemic shock, or physical damage to blood vessels. Indeed, the very invasive methods used to diagnose and treat vascular disease, (e.g. vascular grafts, exploratory and in-dwelling catheters, stents, shunts, and other devices) themselves, damage vessel walls. This can activate plateles, stimulate aggregation, and ultimatly lead to the formation of thrombi and emboli, further endangering the life and health of the patient. Thus, methods for controling or reducing platelet aggregation and clot formation has been a long-sought goal in managing these diseases.

As a result of this increasing understanding of the physiology of platelet aggregation and clot formation, the traditional antithrombotics, aspirin, heparin, and ticlopidine, are increasingly being replaced or supplemented with new agents. One agent of great interest blocks the function of another platelet bound receptor GPIIb-IIIa. GPIIb-IIIa is the major platelet-specific integrin. It is activated by common platelet agonists such as thrombin and histamine to bind fibrinogen and von Willebrand factor. This ligand binding promotes platelet aggregation and the resulting thrombogenic. cascade. Various therapeautics designed to block GPIIb-IIIa activation have focused on the specificity of the ligand-receptor interaction.

It has been determined that the GPIIb-IIIa binding site recognizes the amino acid sequence, arginine-glycine-aspartate (RGD), which is found in a number of thrombogenic activators including fibrinogen and von Willebrand factor.

Consequently, blocking this site inhibits platelet aggregation by preventing the receptor-ligand interaction. Although only 9 of the 20 known integrins recognize the RGD sequence, a major focus in the art has been to block ligand binding to the platelet specific GPIIb-IIIa receptor with peptides containing RGD. Because the RGD peptides appear to have poor stability and a short half life, RGD peptide derivatives, and non-peptide RGD mimetics are currently under development. In addition, GPIIb-IIIa antagonistic drugs based on a number of snake venom proteins with high affinity for the receptor are also under development. Each of these approaches is reviewed in Coller et al., Thrombosis and Haemostasis 74(1):302–308 (1995); and Windsteffer et al., Fibrinolysis & Proteolysis 11 (suppl. 1):85–96 (1997).

Clinically, the most successful GPIIb-IIIa inhibitor to date has been the Fab fragment of the mouse/human chimeric antibody, 7E3 (generic name abciximab; marketed under the tradename ReoPro™ by Eli Lilly and Centocor), which apparently blocks ligand-receptor interactions, including the interaction of GPIIb-IIIa with fibrinogen. (Coller et al., Blood 66:1456–59 (1986)). 7E3 is a potent inhibitor of platelet function and shows promise in reducing ischemic events after angioplasty and other invasive vascular events. Unfortunately, blocking GPIIb-IIIa, as with abciximab, has been associated with profound thrombocytopenia and increased incidents of hemorrhagic complications, including intracranial bleeding. (Bailey et al., Cath. and Cardiovas. Diag. 42:181–84 (1997).

Consequently, there remains a need in the art for safe and efficacious inhibitors of specific platelet functions. Recent research has thus focused on the platelet-specific collagen receptors. As discussed above, GPIV is an unlikely candidate for study due to the apparently minor contribution this receptor makes towards platelet function in vivo. Of the remaining collagen receptors, it is noted that the bleeding disorders associated with GPIIb-IIIa deficiencies are generally more severe than those associated with the lack of GPVI. Therefore, it is expected that blocking GPVI functions would provide the safer clinical alternative. Furthermore, antagonists of GPVI would be preferred over GPIIb-IIIa antagonists because GPVI is more intimately associated with the activation cascade, whereas GPIIb-IIIa is more prominently associated with aggregation leading thrombosis. It is therefore likely that the selective inhibition of GPVI may inhibit thrombosis without affecting hemostatic plug formation, thus providing new clinical weapons against platelet-mediated disease.

The cloning and sequencing of the integrin GPIIb-IIIa provided powerful tools for the functional dissection of this molecule and allowed for the design of important new therapeutic drugs. However, because GPVI collagen receptor has thus far proven refractory to cloning and sequencing, the understanding of GPVI and the design of specific antagonists against GPVI have been severly hampered. Thus, there is a longstanding need in the art to elucidate the GPVI protein and DNA sequences, to use that knowledge to identify GPVI active sites, design agonists and antagonists for research and therapy, generate GPVI peptides and antibodies directed against those peptides, provide nucleic acid probes, enable the in vivo and ex vivo recombinant production of GPVI sequences, and methods for purification and use of GPVI-containing cells and molecules.

SUMMARY OF THE INVENTION

The present invention addresses these needs by providing a novel method for the purification of GPVI and GPVI peptides; the sequence for GPVI peptides; degenerate oligonucleotides corresponding to portions of the nucleic acid encoding GPVI peptides and a fragment of the GPVI cDNA sequence. The full-length cDNA and genomic sequences can be isolated by well known methods using the GPVI cDNA fragment. The discovery of the cDNA encoding human GPVI polypeptide will enable construction of expression vectors comprising nucleic acid sequences encoding GPVI polypeptides; host cells transfected or transformed with the expression vectors; biologically active human GPVI polypeptide and GPVI as isolated and purified proteins; antibodies that are immunoreactive with GPVI polypeptides and peptides; and methods of using the GPVI sequences for research and therapy. Antibodies, and methods of using the GPVI sequences for research and therapy, can also be derived from the GPVI peptide sequence presented below.

GPVI Purification

The present invention also encompasses a novel and efficient method of purifying GPVI polypeptides. The invention further encompasses the peptides produced from GPVI polypeptides synthetically, by chemical or enzymatic treatment of purified GPVI polypeptides, or by recombinant means. These methods provide isolated GPVI polypeptides suitable for amino acid sequencing and other biochemical studies.

GPVI Polypeptides

The present invention encompasses the predicted amino acid sequences of GPVI peptide fragments shown in Table 1. These fragments are used to construct degenerate oligonucleotide probes and PCR primers for the isolation of GPVI nucleic acids and for the generation of antibodies specific for GPVI.

Degenerate Oligonucleotides

Degenerate oligonucleotides corresponding to the nucleic acids encoding GPVI peptides are used as PCR primers and oligonucleotde probes to isolate GPVI genomic and cDNAs.

Nucleic Acids

The invention encompasses an isolated nucleic acid molecule comprising the DNA sequence of SEQ ID NO:1 and SEQ ID NO:4 and an isolated nucleic acid molecule encoding the amino acid sequence of SEQ ID NOs:2 and 3. The invention also encompasses nucleic acid molecules complementary to these sequences, as well as fragments thereof. As such, the invention includes double-stranded nucleic acid molecules comprising the DNA sequence of SEQ ID NOS:1 and 4, and isolated nucleic acid molecules encoding the amino acid sequence of SEQ ID NOs:2 and 3. Both single-stranded and double-stranded RNA and DNA GPVI nucleic acid molecules are encompassed by the invention. These molecules can be used to detect both single-stranded and double-stranded RNA and DNA variants of GPVI encompassed by the invention. A double-stranded DNA probe allows the detection of nucleic acid molecules equivalent to either strand of the nucleic acid molecule. Isolated nucleic acid molecules that hybridize to a denatured, double-stranded DNA comprising the DNA sequence of SEQ ID NOS:1 OR 4, or an isolated nucleic acid molecule encoding the amino acid sequence of SEQ ID NO:2 or 3 under hybridization conditions of 50% formamide and 6×SSC, at 42° C. and washing conditions of moderate (60° C., 0.5×SSC, 0.1% SDS) or high (68° C., 0.2×SSC, 0.1% SDS) stingency are encompassed by the invention.

The invention further encompasses isolated nucleic acid molecules derived by in vitro mutagenesis from SEQ ID NOs:1 and 4. in vitro mutagenesis would include numerous techniques known in the art including, but not limited to, site-directed mutagenesis, random mutagenesis, and in vitro nucleic acid synthesis. The invention also encompasses isolated nucleic acid molecules degenerate from SEQ ID NOs:1 and 4 as a result of the genetic code and isolated nucleic acid molecules that are naturally occuring or synthetic allelic variants of human GPVI DNA, or GPVI homologs from non-human species. The invention also encompasses recombinant vectors that direct the expression of these nucleic acid molecules and host cells transformed or transfected with these vectors.

Protein Sequences

The invention also encompasses isolated polypeptides and small peptides encoded by these nucleic acid molecules, including isolated polypeptides in glycosylated and non-glycosylated form. Such polypeptides include the full-length amino acid sequence of GPVI disclosed in SEQ ID NO:5 as well as the partial amino acid sequence of GPVI disclosed in SEQ ID NOs:2 or 3, and further include any contiguous peptide sequence of 3, 4, 5, 6, 7, 8, or 9 amino acids disclosed in SEQ ID NOs: 2, 3, or 5, preferably, a peptide sequence of SEQ ID NOs:2, 3, or 5 to which an antibody specific to GPVI can be raised. The invention further encompasses the peptides produced from GPVI polypeptides by chemical or enzymatic treatment or by recombinant or synthetic means.

Vectors and Expression

The present invention also provides recombinant expression vectors comprising the GPVI DNA sequences defined herein, recombinant GPVI expression molecules produced using the recombinant expression vectors, and processes for producing the recombinant GPVI molecules using the expression molecules. Such processes encompass methods for the production of GPVI polypeptides including culturing a host cell under conditions promoting expression and recovering the polypeptide from the culture medium. The expression of GPVI polypeptides, including fusion proteins, in bacteria, yeast, plant, and animal cells is encompassed by the invention.

Antibodies

Isolated polyclonal or monoclonal antibodies, including fragments thereof, that bind to a human GPVI polypeptide are encompassed by this invention. Such antibodies may be generated by immunization of an animal with purified naturally-produced, recombinant or synthetic human GPVI polypeptide or peptide, including peptides having any of the sequences shown in Table 1. Alternatively, GPVI specific antibodies may be generated in vitro. Anti-GPVI antibodies further encompass humanized, or otherwise chimeric, antibodies wherein the antigen binding domain recognizes an epitope of GPVI. Isolated polyclonal or monoclonal antibodies that bind to a human recombinant or synthetic GPVI polypeptide and purified by binding with human GPVI polypeptide or peptide are also encompassed by this invention.

Assays

In addition, the present invention provides compositions for use in therapy, diagnosis, and assay of GPVI and GPVI function. Such compositions and methods comprise effective quantities of GPVI polypeptides, or antibodies directed against GPVI polypeptides, to screen for and identify GPVI ligand binding sites, potential inhibitors or activators of activity associated with GPVI ligand binding sites, and methods of using GPVI polypeptides, antibodies and GPVI inhibitors and activators as therapeutic agents for the treatment of diseases or conditions mediated by GPVI-dependent activation. Methods of using GPVI polypeptides in the design of inhibitors and/or probes of GPVI functions are specifically an aspect of the invention.

Therapeutic Compounds

Also included in the present invention are soluble peptides, including GPVI peptides; anti-GPVI antibodies and antibody fragments; GPVI ligands; and antagonists which can be useful as therapeutic agents in inhibiting GPVI ligand binding, signal transduction, and/or platelet activation.

BRIEF DESCRIPTION OF THE DRAWINGS

This invention will be more fully described with reference to the drawings in which:

FIG. 1 illustrates a novel method for purifying GPVI and GPVI peptides.

FIG. 2 illustrates the nucleotide sequence and amino acid translations of a GPVI cDNA fragment. Nucleotides corresponding to the reverse primer for Peptide 5 are underlined.

FIG. 3 illustrates the nucleotide sequence and corresponding amino acid sequence of the full-length cDNA sequence of GPVI isolated by using the sequence represented by SEQ ID NO:1.

FIG. 5 illustrates the amino acid sequence translated from the coding region of pPICZGPVI. The external domain of GPVI is underlined.

DETAILED DESCRIPTION OF THE INVENTION

Figure 4:
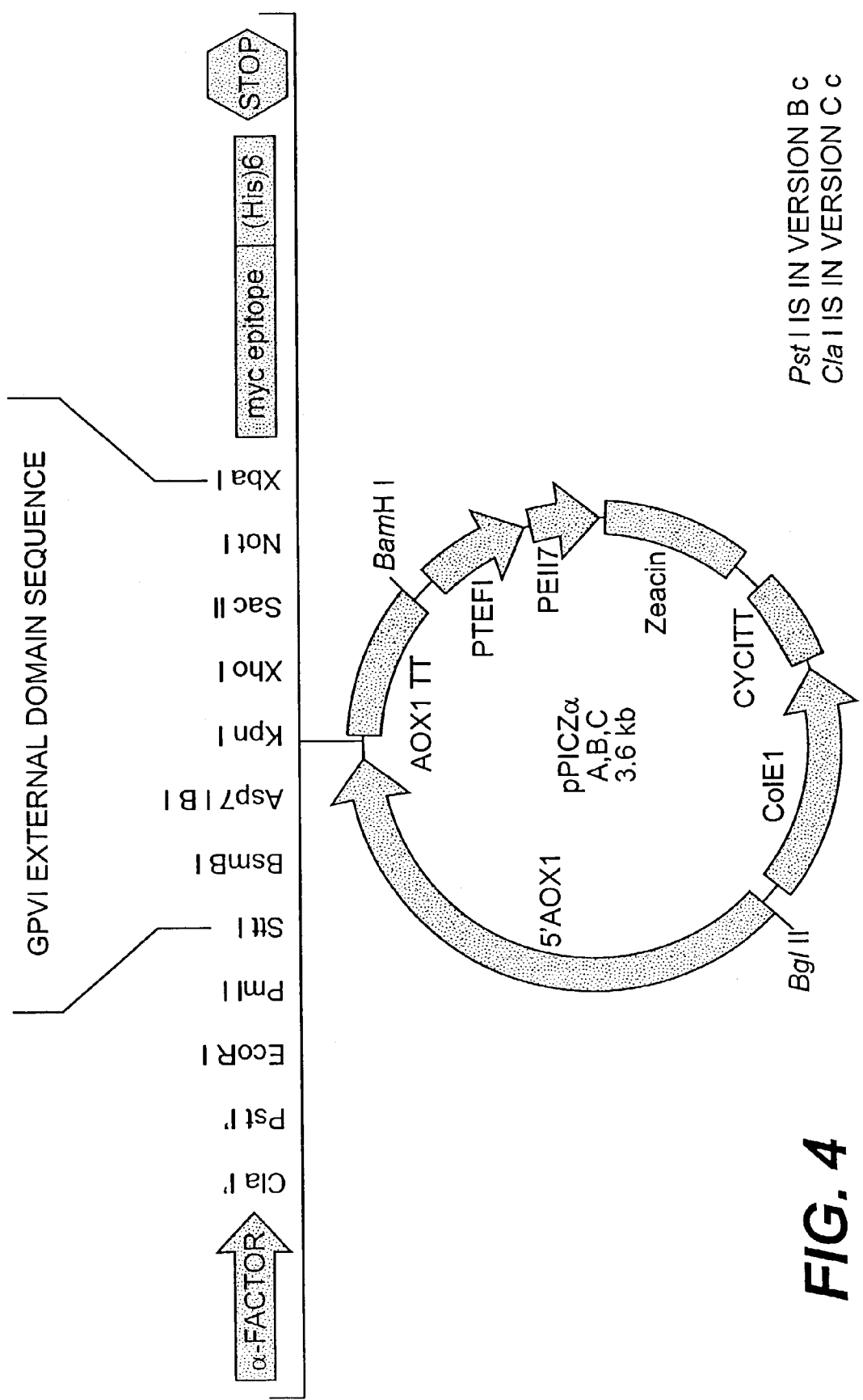
FIG. 4 illustrates the pPICZu, derivative vector, pPICZG-PVI, used to produce soluble recombinant GPVI in yeast.

This invention describes a novel method for the purification of GPVI from human platelets. This method provides sufficiently purified protein to generate the partial amino acid sequence presented in Table 1. This invention further describes the design of degenerate oligonucleotide probes corresponding to the GPVI amino acid sequence and their use in isolating a novel cDNA fragment encoding a portion of the human GPVI polypeptide. With these tools, the full-length cDNA and genomic sequences can be isolated by well known methods. The present discovery of GPVI nucleotide and peptide sequences enables construction of expression vectors comprising nucleic acid sequences encoding GPVI polypeptides; host cells transfected or transformed with the expression vectors; biologically active human GPVI polypeptide and GPVI as isolated and purified proteins; and antibodies immunoreactive with GPVI polypeptides and peptides.

Purification of GPVI from Human Platelets

The novel method for purifying GPVI and GPVI peptides is diagramed in FIG. 1. Specific technical details are provided below.

Preparation of Platelet Suspension

A suspension of concentrated human platelets (American Red Cross), outdated for clinical use, was treated to obtain membrane fraction essentially as described in Tandon et al, J. Biol Chem. 264(13):7570–75 (1989) (incorporated herein by reference.). Briefly, 50 unit equivalents of platelet concentrate, were pooled in 1 liter centrifuge bottles within 10 days of venipuncture. The pooled concentrates were made 5 mM with respect to EGTA and EDTA and 1 mM with respect to benzamidine. The suspension was centrifuged at 3200×g for 5 min at 22° C. in a Sorvall RC-3 centrifuge to sediment red blood cells. The supernatant was removed and further centrifuged at 3200×g for 45–60 min to sediment platelets. The platelets were resuspended and washed twice with Buffer A (140 mM NaCl; 10 mM Tris-HCl; 1 mM each of EDTA, EGTA, and benzamidine; 0.05% NaN3, pH 7.4). The platelet pellets were then suspended in a hypotonic buffer, Buffer B (20 mM Tris.HCL, 1 mM each EDTA, EGTA, benzamidine, PMSF, NEM and sodium venadate, 0.05% azide, pH 7.4) at a final platelet concentration of $1 \times 10^9$/ml to induce cell membrane rupture. At this stage cell suspensions were frozen at −70° C. Frozen platelets were thawed and processed for the preparation of crude membranes as described below.

Membrane Isolation

A cell particulate fraction was obtained from the above platelet suspensions by subjecting them to sonication (five 20-s bursts of sonication on ice (Branson Sonifier, setting 7) followed by centrifugation at 100,000×g at 4° C. The resulting supernatant was discarded and the pellets were resuspended in Buffer B and subjected to a repeat cycle of sonication and high speed centrifugation to ensure complete cell rupture and removal of trapped cytoplasmic contents.

The resulting pellets were suspended in 9 ml of Buffer C (20 mM Tris.HCL; 25 ug/ml leupeptin; 1 mM each of CaCl2, MgCl2, benzamidine, PMSF, NEM and sodium venadate; 0.05% azide; pH 7.4) per unit of platelet of concentrate to generate the crude membrane preparation.

Membrane Solubilization

The crude membrane preparation was solubilized by adding 1/10th volume of a 10% solution of Triton X-100 in water at 4° C. with stirring. The material was stirred overnight at 4° C. followed by centrifugation at 100,000×g for 60 min at 4° C. to remove insoluble material. The Triton-insoluble pellets, comprising a large cytoskeletal component, were discarded and the Triton-soluble fraction, containing platelet membrane glycoproteins and proteins, was used as the starting material for the purification of GPVI.

Purification of GPVI from the Triton-Soluble Supernatant

Concanavalin A-coupled agarose (ConA) (150 ml packed gel) and Wheat Germ Agglutunin-agarose (WGA) (100 ml packed gel) from Vector Laboratory, CA. were packed in columns (Pharmacia, Sweden) and equilibrated in Buffer D (20 mM Tris. HCl, pH 7.4; 1 mM CaCl2; 1 mM MgCl2; 0.05% NaN3; and 0.1% Triton X-100). The inlet of the ConA column was connected to a pump and the outlet was connected to the inlet of the WGA column as shown in FIG. 1.

On sodium dodecyl sulfate-polyacrylamide gel electrophorisis (SDS-PAGE), both glycosylated albumin and al antitrypsin migrate very close to GPVI. Thus, the ConA column was arranged in tandem with the WGA column to adsorb majority of GPIIb-IIIa, GPIV, glycated albumin and α1 antitrypsin on ConA column and enrich the lysate in GPVI for adsorption by the WGA-agarose beads.

The Triton-soluble membrane fraction (~500 ml) was introduced through the ConA column at a flow rate of 0.25 ml/min at 4° C. The unbound fraction from the ConA column passed directly through the WGA column and the flow-through from the WGA column was discarded.

Both columns were washed extensively with Buffer E (Buffer D in which Triton X-100 has been replaced with Triton X-100R and supplemented with 1 M NaCl) to remove non-specifically bound proteins and replace Triton X-100 with Triton X-100R (a non-UV adsorbing detergent). The columns were disconnected and eluted with respective sugars to elute bound glycoproteins (GPs) from each column. In case of WGA-agarose, the bound GPs were eluted with Buffer E containing 250 mM N-acetyl glucosamine but lacking 1 M salt. The ConA column was similarly eluted with Buffer E containing 250 mM α-methyl mannoside.

Eluate fractions were collected an analyzed by SDS-PAGE followed by electrotransfer and Western blotting with antibodies to GPVI, IIb-IIIa and GPIV. Western analysis of the eluted fractions showed that the majority of GPIIb-IIIa and GPIV is captured by the ConA column whereas GPVI binds preferentially to the WGA columns.

The GPVI enriched WGA-eluate was adsorbed onto a Fast Flow Q Sepharose (75–100 ml) column equilibrated in 20 mM Tris.HCl, 0.1% Triton X-100R, 0.05% NaN3 (Buffer F) at a flow rate of 3 ml/minutes. The column was washed with the equilibration buffer and sequentially eluted with Buffer F containing 150, 250, 500, and 1000 mM salt (100 ml for each salt concentration). GPVI eluted from the column with 500, and 1000 mM salt buffers but not with 150, and 250 mM salt.

Fractions containing GPVI were pooled and dialyzed against 20 mM Tris.HCl, pH 7.4 to remove salt. The dialyzed fraction was then adsorbed (flow rate 1 ml/min) over a MonoQ column (10 ml) equilibrated in Buffer F. The column was washed with Buffer F, in which Triton X100R has been replaced with 0.3% octylglucoside (OG) until the optical density of the flow through returned to the baseline value. The bound material was eluted with Buffer F-OG containing 1 M salt, concentrated down to 5 ml volume using a PM10 filter (Amicon filtration assembly), and dialyzed against TBS (10 mM Tris. HCl; 150 mM NaCl; pH 7.5) to reduce salt.

Convulxin-Agarose Affinity Chromatography

An affinity matrix to selectively adsorb GPVI was generated by covalently coupling convulxin to activated sepharose beads. Convulxin was purified as described in Polgar et al., J. Biol. Chem. 272(24):13576–83 (1997), from *Crotalus Durissus Terrificus* snake venom (Soerenson Laboratories, Brazil). Briefly, purified convulxin was coupled to CH-activated Sepharose (Pharmacia) at a concentration of 2 mg convulxin/ml packed gel as described by the manufacturer.

The convulxin-coupled beads (8 mL) were washed with TBS containing 0.3% OG and incubated with MonoQ eluted-TBS dialyzed fraction with gentle rotation overnight at 4° C. The unbound and non-specifically bound components were removed by extensive washing of the beads with TBS-OG buffer containing 1 M NaCl.

The high affinity bound components were eluted by incubating the convulxin-beads with low pH buffer (200 mM acetic acid, 0.5 M salt, 0.5% OG, pH 2.5) for 30 minutes. The acidic eluate fractions were dialyzed extensively against water, freeze dried and reconstituted in 250 μl 1% SDS for preparative SDS-PAGE.

Preparative Gel Electrophoresis and Western Blotting

110 μl of the convulxin-sepharose eluate was applied to each of two lanes of a 20×20×0.15 cm SDS-PAGE gel. Molecular weight markers and 10 μl eluate aliquots were applied to two pairs of wells well separated from the 120 μl lanes. Samples were run at 90 volts for 2 hrs followed by at 250 volts at 4° C. until the dye front reached at the bottom. The resolved proteins were transferred on to nitrocellulose sheet as described in Tandon et al., *J. Biol Chem.* 264: 7570–75 (1989). The nitrocellulose sheet was cut into strips and portions containing a molecular weight marker lane and a 10 ul sample were probed with either biotinylated convulxin or with anti-GPVI human IgG to visualize the position of GPVI band on the blot. The migration of convulxin-reactive and anti-GPVI positive bands was calculated relative to the molecular weight markers.

To visualize protein bands on the blot, the portion of the blot with 120 ul material/lane was stained with a reversible dye, Ponceau stain, for 2 minutes and then briefly destained with water to reduce background. Ponceau positive bands were marked with a blunt pencil. Two major bands became visible by Ponceau staining: a diffused broad band of 74–92 kDa having an average molecular size of about ~84 kDa, and a sharply defined band around ~59 kDa.

Comparison to the Western blot results indicated that the Ponceau-stained bands reacted with both convulxin and anti-GPVI antibody. However, the Ponceau positive sharp band at 59 kDa, when probed with convulxin and anti-P62 antibody showed a broader band ranging from 52–59 kDa in size. This band was divided into two parts: the top half (strongly positive with the dye) was designated band #2 and represents intact GPVI. The lower portion, designated band #3, was lightly stained with Ponceau dye but reacted strongly with convulxin. Band #3 appears to be a GPVI degradation product generated during the purification process. The band at 84 kDa site was designated band #1. Bands #1–3 were excised from the blot and stored at 4° C. in moist atmosphere until subjected to micro sequencing.

Partial Amino Acid Sequence of Human GPIV

The excised protein bands were digested with Endoproteinase Lys-C essentially as described in Aebersold, et al. *Proc. Natl. Acad. Sci. USA*, 84:6970–74 (1987). Briefly, each nitrocellulose band was cut into approximately 1–3 mm pieces and washed briefly with 200 μM NaOH and rinsed with MilliQ water. The pieces were then incubated at 37° C. in 0.5% PVP-40, 100 mM Acetic Acid for 30 min. Excess PVP-40 was removed by extensive washing in MilliQ water (at least 10 washes).

Digestion was carried out by incubating the nitrocellulose pieces for 16 hours at 37° in a solution of 0.5–1 μg of endoproteinase LysC (Boehringer Mannheim) in 100 μl of 25 mM Tris-HCl pH 8.5, 1 mM EDTA. After incubation the nitrocellulose pieces were subjected to sonication for 5 min. The buffer containing the digestion products was removed, the nitrocellulose is washed with 0.1% TFA (trifluoroacetic acid) and then combined with the digestion products. Particulates were removed by centrifugation at 10,000×g for 5 min. The supernatant was then applied to rpHPLC to separate the peptide fragments.

Automated Edman degradations of the isolated fragments was done using an Applied Biosystems model 477A protein sequences. Phenylthiohydantoin amino acid derivatives were identified using an Applied Biosystems model 120 on-line PTH analyzer to generate the following amino acid sequences.

TABLE 1

Amino Acid Sequence of Isolated Peptides

Peptide 1     X--V--L--A--R--R--Y--R--P--S--Y--Q--D--L--L
(from band #2)    T--L         Q        P     V        X Peptide 2     X--F--T--A--G--R--Y--G--P--X
(from band #2)    V--L Peptide 3     P--S--L--Q--A--L--P--S--S--L--V--P--F--I--T--A--X
(from band #2) L--R--E--Y--R--Y--Q--N--Q--A--I         Y     R
                            F                           E Peptide 4     K--X--V--L--A--R--R--Y--R--P--P--Y--Q--D--L--Y--R--X--E--K
(from band #3)

Peptide 5     K--L--D--X--X--R--Y--Q--D--Q--A--V--L--F--I--P--A--M--K
(from band #3)

Peptide A6    X--L--M--E--N--F--T--A--F--V--D--X
(from band #2) T--A--H--L--R--Q--V--Y--X--L--M--A--X
                  V                       E
                                          G Peptide A7    L--V--N--E--L--T--F
(from band #2)

Peptide A8    D--A--I--P--E--N--L--P--P--L--T--A--D--F--A--E--X--X
(from band #2)

Peptide 9     K--P--S--L--Q--A--L--P--S--S--L--V--P--L--E--K
(from band #3)

Peptide 10    K--P--S--L--Q--A--L--P--S--S--L--V--P--F--I--T--A--X
(from band #2)

TABLE 1-continued

Amino Acid Sequence of Isolated Peptides

Peptide 11      K--L--S--S--S--R--Y--Q--D--Q--A--V--L--F--I--P--M--A--K
(from band #3)

Peptide 12      K--L--D--X--X--R--Y--Q--D--Q--A--V--L--F--I--P--M--A--K
(from band #2)

Table 1 depicts the amino acid sequence data of isolated bands #2 and #3. The strongest signals at each position are indicated in bold-face type. X represents an undetermined amino acid at a position. Peptides 1–5 and 9–12 represent novel peptides without apparent homology to published sequences. Peptides 1 and 4, obtained from protein bands #2 and #3, respectively, have highly related sequences, suggesting that band #3 is a degradation product of the higher molecular weight band #2. Similarly, peptide pairs 9–10 and 11–12 also show highly related amino acid sequences which suggest that band #3 is derived from band #2.

Peptides A6–A8 show some similarity with bovine and human albumins but may represent previously undescribed proteins. The sequence of Peptide A6 may be derived from a mixture of two albumin-like peptides.

Generation of Degenerate Oligonucleotide Probes

Degenerate oligonucleotides were designed to correspond to the nucleic acids encoding peptide fragments shown in Table 1. These oligonucleotides were used as probes to isolate GPVI genomic and cDNAs from human libraries and as PCR primer pairs to isolate GPVI cDNAs encoding the peptides shown in Table 1.

A full length GPVI cDNA is isolated by probing an appropriate recombinant cDNA library with the isolated genomic or cDNA fragment using standard methods, as taught, for instance, in Sambrook et al. *Molecular Cloning: A Laboratory Manual,* 2 ed. Vol. 1, pp. 1.101–104, Cold Spring Harbor Laboratory Press, (1989). Suitable cDNA libraries include those generated using bone marrow, platelet, or megakaryocyte (e.g., cell line K562) mRNA.

Isolation of GPVI cDNA Fragments Using Degenerate PCR Primers

Degenerate PCR primers were designed to amplify the predicted nucleic acid sequences encoding the peptides described in Table 1 according to the methods of Sambrook et al. *Molecular Cloning: A Laboratory Manual,* 2 ed. Vol. 1, pp. 11.3–11.19, Cold Spring Harbor Laboratory Press (1989). The following primers correspond to the bold-faced portion of peptides 1, 2, and 5:

Forward primers for Peptide 1   (K X V L A R R Y R P S(P) Y Q D L L)

GPVIF2:     5'-GNM GNT AYM GNC CNH SNT AYC ARG A-3'

GPVIF2S:    5'-GNT AYM GNC CNH SNT AYC ARG A-3'

Forward primer for Peptide 2    (K X F T A G R Y G P X)

GPVIF1:     5'-TTY ACN GCN GGN MGN TAY GGNCC-3'

Forward primer for Peptide 5    (K L D X X R Y Q D Q A V L F I P A M K)

GPVIF3:     5'-YTN TTY ATH CCN GCN ATG AAR-3'

Reverse primer for Peptide 5    (K L D X X R Y Q D Q A V L F I P A M K)

GPVIR:      5'-NAR NAC NGC YTG RTC YTG RTA-3'

Degenerate PCR primers were used to amply GPVI-specific cDNA using standard methods using Marathon-Ready human bone marrow CDNA kit (Cat.#: 7416-1, Clontech). The mRNA used to construct this bone marrow CDNA kit was pooled from 24 male/female Caucasians, ages 17–61. The end of each cDNA is linked to a synthetic adaptor sequence. The cDNA kit provides various adaptor and nested adaptor primers for PCR.

Pairs of adaptor and degenerate primers were used to isolate GPVI cDNA fragments from the bone marrow cDNA pool according to the manufactures instructions. Isolated fragments were cloned into pCRII using an Invitrogen TA cloning kit, according to the supplier's instructions. The sequence of the cloned fragment was determined using standard methods and is presented in FIG. 2 and SEQ ID NO: 1. The longest open reading frame includes an exact match to the sequence of Peptide 9. The carboxy-terminus of the translated sequence is also highly similar to Peptide 11, with the exception that the sequence SSSRYQ (SEQ ID NO:29) of the peptide is SSSRYH (SEQ ID NO:30) in the translation. This difference may represent a naturally-occurring variant. Alternatively, because the reverse PCR primer used to isolate the DNA was degenerate at this position, the difference may reflect a cloning artifact. The presence of a stop codon preceding the presumptive reading frame suggests that the isolated cDNA encodes the amino-terminus of GPVI.

Cloning of Full-Length cDNA of Human GP VI

The full-length cDNA of human GPVI was isolated by PCR using the information obtained from the 240 bp PCR fragment represented in SEQ ID NO: 1. The initiation site was identified as beginning at the ATG codon at base 17

(base-numbering according to SEQ ID NO:1) due to an in-frame stop codon TGA at base 8. A forward PCR primer was synthesized based on SEQ ID NO:1 from bases 14 to 33 (5'CCCACCATGTCTCCATCCCCGAC3') (SEQ ID NO: 31) and the T7 primer (5'GTAATACGACTCACTAT-AGGGC3') (SEQ ID NO: 32) was used as a reverse PCR primer. PCR was performed on a phagemid human platelet cDNA library which was constructed into the Lambda ZAP II vector (Stratagene) and which was a gift from Dr. G. Roth at the University of Washington, Division of Hematology. Two fragments of sizes ~1.7 and 2.0 kb were amplified. Subsequent cloning of the two PCR fragments into the PCRII vector (Invitrogen) followed by DNA sequencing (with an ABI 377 automatic DNA sequencer) confirmed that the 1.7 kb fragment contained the 240 bp sequence represented by SEQ ID NO:1. The longest open reading frame encompasses nucleotides 17 to 1036 and contains an additional 645 bp non-coding region in the 3' end. The full-length cDNA sequence including the 3' non-coding region of the instant invention is represented by SEQ ID NO:4 and its corresponding amino acid sequence is represented by SEQ ID NO:5 and are both shown in FIG. 3.

The 3' non-coding region of GPVI mRNA may have regulatory activity that affects the stability, transcription, and transport of mRNA. Recent reviews discussing the regulatory function of 3' untranslated regions can be found in Standart and Jackson, *Biochimie* 76:867–879 (1994), St. Johnston, *Cell* 81:161–170 (1995), and in Beelman and Parker, *Cell* 81:179–183 (1995). For example, while the 3' non-coding region of some transcripts have been implicated in stabilizing mRNA, some short-lived or unstable cellular mRNAs have been shown to contain an A and U-rich (AU-rich) region within the 3' untranslated region (3' UTR) that induces rapid mRNA degradation. These cellular genes containing destabilizing sequences include genes encoding granulocyte-monocyte colony stimulating factor (GM-CSF) (Shaw, and Kamen, *Cell* 46:659–667 (1986)) and the myc proto-oncogene (c-myc) (Cole and Mango, *Enzyme* 44:167–180 (1990)). Other unstable or short-lived mRNAs which have been shown to contain AU-rich sequences within the 3' UTR include interferons (alpha, beta and gamma IFNs), interleukins (IL1, IL2 and IL3), tumor necrosis factor (TNF), lymphotoxin (Lym), IgG1 induction factor (IgG IF), granulocyte colony stimulating factor (G-CSF), myb proto-oncogene (c-myb), and sis proto-oncogene (c-sis) (Shaw, and Kamen, *Cell* 46:659–667 (1986).

The 3' untranslated region may also contain elements that regulate mRNA transport from the nucleus to the cytoplasm. In most cases, cellular mRNAs contain introns that are removed by splicing before transport to the cytoplasm occurs. Transport to the cytoplasm is required for the mRNA to interact with the ribosomes and accessory factors in the process of protein synthesis. Recent studies have suggested that intron-containing RNAs are usually prevented from exiting the nucleus due to the binding of splicing factors (Chang and Sharp, *Cell* 59:789–795; 1989; Legrain and Rosbash, *Cell* 57:573–583, 1989). While the exact export mechanism(s) that allow these mRNAs to be transported has yet to be elucidated, recent data indicates that different RNA species may share common steps in the export pathway. In that regard, export is believed to involve targeting to the sites of exit and transport through them, probably as a RNA-protein complex. Thus, the cellular pathway of nucleocytoplasmic transport of mRNA includes a factor (one or more proteins), intrinsic to the cell, which binds to a sequence(s) contained in the mRNA. One such example is the constitutive transport enhancer (CTE) located in the 3' untranslated region of the Mason Pfizer Monkey Virus (MPMV) (Pasquinelli et al., *EMBO J* 16(24):7500–10, 1997). It seems likely that this genetic enhancer allows MPMV to tap into a constitutive cellular pathway, by interacting with a cellular factor that plays a role in mRNA transport that is normally used for the transport of cellular mRNA from the nucleus to the cytoplasm.

It is therefore possible to identify GPVI nucleic acid sequences by hybridization of nucleic acid probes to the 3' non-coding region. Nucleic acid probes within the scope of the invention include synthetic or isolated DNA and RNA sequences containing all or part of the 3' non-coding sequence of GPVI. Hybridization can be performed under moderate or high stringency conditions, which are known to those having ordinary skill in the art. As used herein, conditions of moderate stringency, as known to those having ordinary skill in the art, and as defined by Sambrook et al. *Molecular Cloning: A Laboratory Manual*, 2 ed. Vol. 1, pp. 1.101–104, Cold Spring Harbor Laboratory Press (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of about 60° C., 0.5×SSC, 0.1% SDS. Conditions of high stringency are defined as hybridization conditions as above, and with washing at 68° C., 0.2×SSC, 0.1% SDS. The skilled artisan will recognize that the temperature and wash solution salt concentration can be adjusted as necessary according to factors such as the length of the probe.

Nucleic Acids

Nucleic acid sequences within the scope of the invention include synthetic or isolated DNA and RNA sequences that hybridize to the native GPVI nucleotide sequences under conditions of moderate or severe stringency, as defined above, or which encode GPVI polypeptides. Nucleic acid molecules within the scope of the invention include sequences that hybridize to GPVI DNA under hybridization and wash conditions of 5°, 10°, 15°, 20°, 25°, or 30° below the melting temperature of the DNA duplex of GPVI DNA (SEQ ID NO:1), or of the 3' non-coding region, beginning at nucleotide 1037 of SEQ ID NO: 1.

The invention also encompasses isolated fragments and oligonucleotides encoding the polypeptides of Table 1. Preferable fragments and oligonucleotides are 10–15, 15–20, 20–30, 30–40, and 40–55 nucleotides in size.

Due to the known degeneracy of the genetic code, wherein more than one codon can encode the same amino acid, a DNA sequence can vary from that shown in SEQ ID NO:1 and still encode a GPVI polypeptide having the amino acid sequence of SEQ ID NOs:2 or 3. Such variant DNA sequences can result from silent mutations (e.g., occurring during PCR amplification), or can be the product of deliberate mutagenesis of a native sequence. Of course, variants of SEQ ID NO:4 are also possible.

Nucleic acid sequences within the scope of the invention include DNA sequences that vary from SEQ ID NO:1 and SEQ ID NO:4 and encode a polypeptide or peptide that specifically binds antibodies against a GPVI polypeptide.

The invention thus provides equivalent isolated DNA sequences encoding GPVI polypeptides, selected from: (a) DNA derived from the coding region of a native mammalian GPVI gene; (b) cDNA comprising the nucleotide sequence 1–240 of SEQ ID NO:1; (c) cDNA comprising the nucleotide sequence of 1–1681 of SEQ ID NO:4; (d) DNA capable of hybridization to a DNA of (a) under conditions of moderate stringency and which encodes GPVI polypeptides or peptides; (e) DNA capable of hybridization to a DNA of (a) under conditions of high stringency and which encodes GPVI polypeptides or peptides; and (f) DNA which is degenerate, as a result of the genetic code, to a DNA defined in (a), (b), (c), (d) or (e) and which encodes GPVI polypeptides or peptides. Moreover, GPVI polypeptides encoded by such DNA equivalent sequences are also encompassed by the invention.

DNA that is equivalent to the DNA sequence of SEQ ID NO:1 or SEQ ID NO:4 will hybridize under moderately stringent conditions to the double-stranded native DNA sequences that encode polypeptides comprising amino acid sequences of Peptides 1–6 or 9–12, or amino acids 1–74 of SEQ ID NOs:2 or 3. In another embodiment, this DNA will also hybridize under high stringency conditions. Examples of GPVI polypeptides encoded by such DNA, include, but are not limited to, GPVI polypeptide fragments and GPVI polypeptides comprising inactivated N-glycosylation site(s), inactivated protease processing site(s), or conservative amino acid substitution(s), as herein. GPVI polypeptides or peptides encoded by DNA derived from other mammalian species, wherein the DNA will hybridize to the complement of the DNA of SEQ ID NO:1 or SEQ ID NO:4 are also encompassed.

GPVI DNA, GPVI polypeptides, and antibodies against GPVI polypeptides can be used as reagents in a variety of research protocols. A sample of such research protocols are given in Sambrook et al. *Molecular Cloning: A Laboratory Manual,* 2 ed. Vol. 1–3, Cold Spring Harbor Laboratory Press (1989). For example, GPVI DNA, including synthetic oligonucleotides encoding one or more of the peptide sequences of Table 1, can be used as a probe to identify and isolate the genomic GPVI sequence, including introns, and control elements and to determine the chromosomal location of GPVI DNA and to map genes in relation to this chromosomal location. GPVI DNA can also be used to examine genetic heterogeneity and heredity through the use of techniques such as genetic fingerprinting, as well as to identify risks associated with genetic disorders. GPVI DNA can be further used to identify additional genes related to GPVI DNA and to establish evolutionary trees based on the comparison of sequences. GPVI DNA and polypeptides can be used to select for those genes or proteins that are homologous to GPVI DNA or polypeptides, through positive screening procedures such as Southern blotting and immunoblotting and through negative screening procedures such as subtraction. Also encompassed by this invention are polymerase chain reaction (PCR) primers which can be used to amplify GPVI DNAs, and hybridization probes specific for GPVI nucleotide sequences.

A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Polypeptides

The present invention encompasses isolated GPVI and its substituent peptides, and variants thereof, in purified and-substantially purified preparations. The invention also encompasses the GPVI polypeptides encoded by the DNA fragments of SEQ ID NO.1 and SEQ ID NO:4. Similarly, the invention encompasses the GPVI polypeptides of SEQ ID NOs.2 and 3, and peptides thereof.

As used herein, the term "GPVI polypeptides" (or GPV peptides) refers to a genus of polypeptides that further encompasses proteins having the amino acid sequence of SEQ ID NOs:2 or 3, as well as those proteins having a high degree of similarity (at least 60% amino acid identity, preferably at least 65%, 70%, 75%, 80%, 90%, or 95% identity) with such amino acid sequences and which proteins are biologically active. In particular, GPVI polypeptides includes the amino acid sequences of corresponding GPVI homologs in non-human animals. In addition, GPVI polypeptides refers to the gene products encoded by SEQ ID NO:1 or SEQ ID NO:4.

The isolated and purified GPVI polypeptide according to the invention has a molecular weight of approximately 62,000 Daltons. It is understood that GPVI polypeptides can be varied by fusing additional peptide sequences to both the amino and carboxyl terminal ends of GPVI polypeptides. Fusions of additional peptide sequences at the amino and carboxyl terminal ends of GPVI polypeptides can be used to enhance expression or immunogenicity of GPVI polypeptides, or aid in the purification of the protein. Deletion of amino acids encompassing the predicted transmembrane and cytoplasmic regions of GPVI polypeptide can result in the production of a soluble form of GPVI polypeptide. The soluble form of GPVI polypeptide can be used to block GPVI signal transduction or platelet activation through the GPVI polypeptide. The use of GPVI peptides to block platelet activation or function can form the basis of research probes into structure-function relationships or as therapeutics.

It is understood that fusions of additional peptide sequences at the amino and carboxyl terminal ends of GPVI polypeptides will alter some, but usually not all, of the peptides of GPVI polypeptides generated by enzymatic or chemical treatment.

It is understood that mutations can be introduced into GPVI polypeptides using routine and known techniques of molecular biology. It is further understood that a mutation can be designed so as to eliminate a site of proteolytic cleavage by a specific enzyme or a site of cleavage by a specific chemically induced fragmentation procedure. It is also understood that the elimination of the site will alter the peptide fingerprint of GPVI polypeptides upon fragmentation with the specific enzyme or chemical procedure.

The term "isolated and purified" as used herein, means that the GPVI polypeptide or peptide is essentially free of association with other proteins or polypeptides, for example, as a purification product of recombinant host cell. The term "substantially purified" as used herein, refers to a mixture that contains GPVI polypeptide or peptide and is essentially free of association with other proteins or polypeptides, but for the presence of known proteins that can be removed using a specific antibody. The term "purified" refers to either the "isolated and purified" form of GPVI polypeptides or the "substantially purified" form of GPVI polypeptides, as both are described herein. The term GPVI protein sequence refers to substantially all of the amino acids of SEQ ID Nos.2, 3 or 5, with or without a signal sequence, or to recombinant fusion proteins comprising such sequence. GPVI polypeptide refers to the GPVI protein sequence or a subset thereof. As used herein, GPVI peptide is used interchangeably with GPVI polypeptide, but peptide generally understood to pertain to short amino acid sequences of about 2 to 30 amino acids.

GPVI Polypeptide Variants and Derivatives

A GPVI polypeptide or peptide "variant" as referred to herein means a polypeptide substantially identical to GPVI polypeptides of Table 1, FIG. 2, and FIG. 3, but which has an amino acid sequence different from that of GPVI polypeptide because of one or more deletions, insertions or substitutions. The variant amino acid sequence preferably is at least 60%, 65%, 70%, 80%, 85%, or 90% identical to a GPVI polypeptide amino acid sequence of Table 1. The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring GPVI variants are also encompassed by the invention. Examples of such variants are proteins that result from alternate mRNA splicing events, from proteolytic cleavage of the GPVI polypeptides, and allelic variants of GPVI polypeptide. Variations attributable to proteolysis include, for example, differences in the N- or C-termini upon expression in different types of host cells, due to proteolytic removal of one or more terminal amino acids from the GPVI Polypeptides (generally from 1–5 terminal amino acids).

GPVI polypeptides can be modified to create GPVI polypeptide derivatives by forming covalent or aggregative conjugates with other chemical moieties, such as glycosyl groups, polyethylene glycol (PEG) groups, lipids, phosphate, acetyl groups and the like. Covalent derivatives of GPVI polypeptides can be prepared by linking the chemical moieties to functional, groups on GPVI polypeptide amino acid side chains or at the N-terminus or C-terminus of a GPVI polypepticle or the extracellular domain thereof. Other derivatives of GPVI polypeptides within the scope of this invention include covalent or aggregative conjugates of GPVI polypeptides, alone, or with other proteins or polypeptides. These derivatives include synthetically-derived aggregates and biologically programed constructs, such as by synthesis in recombinant culture as N-terminal or C-terminal fusions. For example, the conjugate can comprise a signal or leader polypeptide sequence (e.g. the α-factor leader of *Saccharomyces*) at the N-terminus of a GPVI polypeptide. The signal or leader peptide co-translationally or post-translationally directs transfer of the conjugate from its site of synthesis to a site inside or outside of the cell membrane or cell wall.

GPVI polypeptide conjugates can comprise peptides added to facilitate purification and identification of GPVI polypeptides. Such peptides include, for example, poly-His or the antigenic identification peptides described in U.S. Pat. No. 5,011,912 and in Hopp et al., *Bio/Technology* 6:1204, 1988.

In addition, GPVI polypeptitdes or peptides may be chemically or physically conjugated to drugs, proteins, peptides, lipids, carbohydrates, or antigens by methods known to those skilled in. the art. Such conjugation may be particularly useful in maintaining secondary or tertiary conformation, or extending the functional half-life of bioactive GPVI polypeptides. Methods of chemical conjugation are well known to those skilled in the art, and include, in part, coupling through available functional groups (such as amino, carboxyl, thio and aldehyde groups). These techniques include those discussed in Wong, *Chemistry of Protein Conjugate and Crosslinking*, CRC Press (1991); Brenkeley et al. *Brief Survey of Methods for Preparing Protein Conjugates With Dyes, Haptenis and Cross-linking Agents, Bioconjugate Chemistry* 3 #1 (1992); and Hermanson, *Bioconjugate Techniques*, Academic Press, (1996); and U.S. Pat. No. 5,693,326 (Lees).

Protein Expression

DNA encoding the GPVI peptides of Table 1, FIG. 2 and FIG. 3 can be chemically synthesized and inserted in any propagation or expression vector known in the art. Thus, recombinant expression vectors containing a nucleic acid sequence encoding GPVI polypeptides can be prepared using well known methods. For example, the oligonucleotides $$5'\text{CGA CGA TAC CGC CCC}3'$$

$$3'\text{GCT GCT ATG GCG GGG}5'$$

can be annealed and inserted in frame into a restriction site of an appropriate expression vector to program the expression of a portion of Peptide 1. Similarly, nucleotides of SEQ ID NO: 1 which encode the all or part of the peptides of SEQ ID Nos: 2 or 3 can be inserted into an expression vector in the appropriate orientation and reading frame to generate a portion of the GPVI peptide sequence.

Suitable expression vectors include a GPVI DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, mRNA splicing signals, poly A addition signals, and other appropriate sequences which control transcription and translation initiation and termination. Nucleotide sequences are "operably linked" when the regulatory sequence functionally relates to the GPVI DNA sequence. Thus, a promoter nucleotide sequence is operably linked to a GPVI DNA sequence if the promoter nucleotide sequence controls the transcription of the GPVI DNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with GPVI polypeptides can be incorporated into expression vectors. For example, a DNA sequence for a signal peptide (secretory leader) can be fused in-frame a nucleotide sequence encoding a GPVI polypeptide such that the polypeptide is initially translated as a fusion protein comprising the signal peptide. A signal peptide that is functional in the intended host cells enhances extracellular secretion of the GPVI polypeptide. The signal peptide can be cleaved from the GPVI polypeptide upon secretion of GPVI polypeptide from the cell.

Fusion Proteins

In another embodiment of this invention, the expression of recombinant GPVI polypeptides can be accomplished utilizing fusion of a sequence encoding GPVI polypeptides to sequences encoding another polypeptide to aid in the purification of GPVI polypeptides. An example of such a fusion is a fusion of sequences encoding a GPVI polypeptide to sequences encoding the product of the malE gene of the pMAL-c2 vector of New England Biolabs, Inc. Such a fusion allows for affinity purification of the fusion protein, as well as separation of the maltose binding protein portion of the fusion protein from the GPVI polypeptide after purification. It is understood of course that many different vectors and techniques can be used for the expression and purification of GPVI polypeptides and that this embodiment in no way limits the scope of the invention.

The insertion of DNA encoding a GPVI polypeptide into the pMAL-c2 vector can be accomplished in a variety of ways using known molecular biology techniques. The preferred construction of the insertion contains a termination codon adjoining the carboxyl terminal codon of the GPVI polypeptide. In addition, the preferred construction of the insertion results in the fusion of the amino terminus of the GPVI polypeptide directly to the carboxyl terminus of the Factor Xa cleavage site in the pMAL-c2 vector. A DNA fragment can be generated by PCR using GPVI DNA as the template DNA and two oligonucleotide primers. Use of the oligonucleotide primers generates a blunt-ended fragment of DNA that can be isolated by conventional means. This PCR product can be ligated together with pMAL-p2 sequences using conventional means. Positive clones can be identified by conventional means. Induction of expression and purification of the fusion protein can be performed as per the manufacturer's instructions. This construction facilitates a precise separation of the GPVI polypeptide from the fused maltose binding protein utilizing a simple protease treatment as per the manufacturer's instructions. In this manner, purified GPVI polypeptide can be obtained. Furthermore, such a constructed vector can be easily modified using known molecular biology techniques to generate additional fusion proteins. Similar constructs can be derived using the histidine-tag system in which 6 contiguous histidine molecules are incorporated into a GPVI fusion protein. The expressed fusion protein may be partially purified on immobilized nickel.

Host Cells

Suitable host cells for expression of GPVI polypeptides include prokaryotes, yeast, or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce GPVI polypeptides using RNAs derived from DNA constructs disclosed herein.

Prokaryotic-Expression

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a GPVI polypeptide can include an N-terminal methionine residue to facilitate expression of the recombinant polypeptide in the prokaryotic host cell. The N-terminal Met can be cleaved from the expressed recombinant GPVI polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a GPVI DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA). Other commercially available vectors include those that are specifically designed for the expression of proteins; these would include pMAL-p2 and pMAL-c2 vectors that are used for the expression of. proteins fused to maltose binding protein (New England Biolabs, Beverly, Mass., USA).

Promoter sequences commonly used for recombinant prokaryotic host cell expression vectors include β-lactamase (penicillinase), lactose promoter system (Chang et al., Nature 275:615, 1978; and Goeddel et al., *Nature* 281:544, 1979), tryptophan (trp) promoter system (Goeddel et al., Nucl. Acids Res. 8:4057, 1980; and EP-A-36776), and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection, which incorporate derivatives of the λ $P_L$ promoter, include plasmid pHUB2 (resident in *E. coli* strain JMB9 (ATCC 37092)) and pPLc28 (resident in *E. coli* RR1 (ATCC 53082)).

DNA encoding GPVI polypeptides may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli*.

For expression of the recombinant protein, the bacterial cells are propagated in growth medium until reaching a pre-determined optical density. Expression of the recombinant protein is then induced, e.g. by addition of IPTG (isopropyl-b-D-thiogalactopyranoside), which activates expression of proteins from plasmids containing a lac operator/promoter. After induction (typically for 1–4 hours), the cells are harvested by pelleting in a centrifuge, e.g. at 5,000×G for 20 minutes at 4° C.

For recovery of the expressed protein, the pelleted cells may be resuspended in ten volumes of 50 mM Tris-HCl (pH 8)/1 M NaCl and then passed two or three times through a French press. Most highly-expressed recombinant proteins form insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTT. Any material that cannot be dissolved is removed by centrifugation (10,000×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be carried out by a variety of chromatographic methods, such as ion exchange or gel filtration. In some protocols, initial purification may be carried out before refolding. As an example, hexahistidine-tagged fusion proteins may be partially purified on immobilized nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Eukaryotic Expression

Eukaryotic expression is particularly prefered where a glycosylated protein is desired. GPVI polypeptides alternatively can be expressed in yeast host cells, preferably from the *Saccharomyces* genus (e.g., *S. cerevisiae*). Other genera of yeast, such as *Pichia, K. lactis, Schizosaccharomyces pombe* or *Kluyveromyces*, can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980), or other glycolytic enzymes (Hess et al., *J. Adv. Enzyme Reg.* 7:149, 1968 and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657; Fleer et. al., *Gene,* 107:285–195 (1991); and van den Berg et. al., *Bio/Technology,* 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* can be constructed by inserting DNA sequences from pBR322 for selection and replication in *E. coli* (Ampr gene and origin of replication) into the above-described yeast vectors.

The yeast α-factor leader sequence can be employed to direct secretion of a GPVI polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Yeast transformation protocols are known to those of skill in the art. One such protocol is described by Hinnen et al., *Proc. Natl. Acad. Sci. USA* 75:1929, 1978. The Hinnen protocol selects for Trp$^+$ transformants in a selective medium, wherein the selective medium consists of 0.67% yeast nitrogen base, 0.5% casamino acids, 2% glucose, 10 μg/ml adenine, and 20 μg/ml uracil.

Yeast host cells transformed by vectors containing ADH2 promoter sequence can be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant GPVI polypeptides. These systems may be used where it is desired to maintain a glycosylation pattern more similar to that found in the intact platelet. Maintenance of the endogenous glycosylation pattern may be preferred in some applications and may contribute to GPVI stability or to some GPVI functions. The binding activity of recombinantly-expressed membrane bound GPVI and GPVI fusion proteins may be assaysed by expressing a GPVI polypeptide in a non-adherent cell type, such as the CEM T cell line, and testing for adherence to collagen-coated plates, as described in Chiang et al., *J. Clin. Invest.* 100(3):514–21 (1997).

Baculovirus systems for production of heterologous proteins in insect cells are reviewed by Luckow and Summers, *Bio/Technology* 6:47 (1988). Established cell lines of mammalian origin also can be employed. Examples of suitable mammalian host cell lines include the COS-7 line of monkey kidney cells (ATCC CRL 1651) (Gluzman et al., *Cell* 23:175,1981), L cells, C127 cells, 3T3 cells (ATCC CCL 163), Chinese hamster ovary (CHO) cells, HeLa cells, BHK (ATCC CRL 10) cell lines, and the CV-1/EBNA-1 cell line (ATCC CRL 10478) derived from the African green monkey kidney cell line CVI (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, pp. 15–69, 1990). Additional protocols using commercially available reagents, such as Lipofectamine (Gibco/BRL or Lipofectamine-Plus, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. *Molecular Cloning: A Laboratory Manual*, 2 ed. Vol. 1–3, Cold Spring Harbor Laboratory Press (1989). Selection of stable transformants can be performed using resistance to cytotoxic drugs as a selection method. Kaufman et al., Meth. in Enzymology 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind IIII site toward the BgI I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529–534) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, (1996). Expression of a heterologous cDNA as part of a dicistronic mRNA followed by the gene for a selectable marker (eg. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type H IL-1 receptor signal peptide described in EP 460,846.

With respect to any of the above-listed techniques, a protease cleavage site can be inserted between the GPVI sequence and the non-homologous portion of the fusion protein. Thus, if it is necessary to a remove a Histidine tag, for example, from the purified protein, a protease cleavage site can be inserted between the hexahistidine sequence and the GPVI sequence. Enterokinase, for example, recognizes the sequence "DDDK" ($Asp_3$-Lys) (SEQ ID NO: 34), and cleaves after the lysine. Alternatively, Carboxypeptidase A can be used for the removal of C-terminal His tags. This enzyme efficiently removes aromatic C-terminal residues (Hoculi, E. Chemische Industrie. 12:69 (1989)) until it encounters a basic residue, at which point removal is terminated.

Purification of Recombinantly Produced GPVI Polypeptides

An isolated and purified GPVI polypeptide according to the invention can be produced by recombinant expression systems as described above. GPVI polypeptides can be substantially purified, as indicated by a single protein band upon analysis by SDS-polyacryl amide gel electrophoresis (SDS-PAGE).

One process for producing GPVI polypeptides comprises culturing a host cell transformed with an expression vector comprising a DNA sequence that encodes a GPVI polypeptide under conditions sufficient to promote expression of the GPVI polypeptide. GPVI polypeptide is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify GPVI polypeptides. Some or all of the foregoing purification steps, in various combinations, are well known and can be employed to provide an isolated and purified recombinant protein.

It is possible to utilize an affinity column comprising a GPVI polypeptide-binding protein, such as a convulxin, (a venom component from the tropical rattlesnake *Crotalus durissus terrificus*, which specifically binds to GPVI with high affinity) (Polgar et al., *J. Biol. Chem.* 272(24):13576–83 (1997), or with a monoclonal antibody generated against GPVI polypeptides, to affinity-purify expressed GPVI polypeptides. GPVI polypeptides can be removed from an affinity column using conventional techniques, e.g., in a high salt elution buffer and then dialyzed into a lower salt buffer for use or by changing pH or other components depending on the affinity matrix utilized.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express GPVI polypeptides as a secreted polypeptide in order to simplify purification. Urdal describes sequential reversed-phase HPLC steps for purification of recombinant human IL-2 on a preparative HPLC column. Urdal et al. (*J. Chromatog.* 296:171, 1984). Secreted recombinant GPVI polypeptide from a yeast host cell fermentation can be purified by analogous methods.

Generation of GPVI Polypeptides

GPVI peptides can be generated synthetically or be generated by chemical fragmentation of a purified GPVI polypeptide. For example, isolated and purified GPVI polypeptide can be treated with cyanogen bromide under conventional conditions that result in fragmentation of the GPVI polypeptide by specific hydrolysis on the carboxyl side of the methionine residues within the GPVI polypeptide (Gross, Methods in Enz. 11:238–255, 1967). Chemical fragmentation includes the use of cyanogen bromide to cleave under neutral or acidic conditions such that specific cleavage occurs at methionine residues (Gross, Methods in Enz. 11:238–255,1967). This can further include further steps, such as a carboxymethylation step to convert cysteine residues to an unreactive species. It is understood of course that many chemicals could be used to fragment GPV1 polypeptides and that this embodiment in no way limits the scope of the invention.

In another embodiment, GPVI peptides can be generated from GPVI polypeptide using enzymes that cleave the polypeptide at specific amino acid residues. An isolated and purified GPVI polypeptide can be treated with Achromobacter protease I under conventional conditions that result in fragmentation of the GPVI polypeptide by specific hydrolysis on the carboxyl side of the lysine residues within the GPVI polypeptide (Masaki et al., Biochim. Biophys. Acta 660:44–50, 1981; Masaki et al., Biochim. Biophys. Acta 660:51–55, 1981). Enzymatic fragmentation includes the use of a protease such as Asparaginylendopeptidase, Arginylendopeptidase, Achrombobacter protease 1, Trypsin, Staphlococcus aureus V8 protease, Endoproteinase Asp-N, or Endoproteinase Lys-C under conventional conditions to result in cleavage at specific amino acid residues. Asparaginylendopeptidase can cleave specifically on the carboxyl side of the asparagine residues present within GPVI polypeptides. Arginylendopeptidase can cleave specifically on the carboxyl side of the arginine residues present within GPVI polypeptides. Achrombobacter protease I can cleave specifically on the carboxyl side of the lysine residues present within GPVI polypeptides (Sakiyama and Nakat, U.S. Pat. No. 5,248,599; Masaki et al., Biochim. Biophys. Acta 660:44–50, 1981; Masakiet al., Biochim. Biophys. Acta 660:51–55, 1981). Trypsin can cleave specifically on the carboxyl side of the arginine and lysine residues present within GPVI polypeptides. Staphlococcus aureus V8 protease can cleave specifically on the carboxyl side of the aspartic and glutamic acid residues present within GPVI polypeptides (Cleveland, J. Biol. Chem. 3:1102–1106, 1977). Endoproteinase Asp-N can cleave specifically on the amino side of the asparagine residues present within GPVI polypeptides. Endoproteinase Lys-C can cleave specifically on the carboxyl side of the lysine residues present within GPVI polypeptides. Other enzymatic and chemical treatments can likewise be used to specifically fragment GPVI polypeptides. It is understood of course that many enzymes could be used to fragment GPVI polypeptides and that this embodiment in no way limits the scope of the invention.

Synthetic GPVI polypeptides and peptides can be generated by a variety of conventional techniques. Such techniques include those described in Merrifield, Methods Enzymol. 289:3–13, 1997; Ball and Mascagni, Int. J. Pept. Protein Res. 48:31–47, 1996; Molina et al., Pept. Res. 9:151–155, (1996); Fox, Mol. Biotechnol. 3:249–258, 1995; and Lepage et al., Anal. Biochem. 213: 40–48, (1993), each of which is incorporated herein by reference.

Immunogenic GPVI polypeptides and peptides are encompassed by the invention. The immunogenicity of GPVI peptides and polypeptides can be determined by conventional techniques, such as those described in *Antibodies: A Laboratory Manual*, Harlow and Lane (eds.), Cold Spring Harbor Laboratory Press, 1988. Immunogenic GPVI polypeptides and peptides are at least 4 amino acids in length. Moreover, antigenic epitopes generally contain about five amino acid residues. (Ohno et al., Proc. Natl. Acad. Sci. USA 82:2945 (1985). However, it is preferred that where monoclonal antibodies are generated against the selected polypeptide or peptide, that the resulting antibodies are specific for GPVI, most preferably, human GPVI. Whether a given fragment is antigenic can be readily determined by routine experimentation. Some peptides may act as haptens or otherwise be poorly immunogenic themselves. It is therefore prefered that peptides be rendered more immunogenic by cross-linking or by coupling to an immunogenic carrier molecule. Appropriate carrier molecules are well known in the art and include keyhole limpet hemocyanin, mammalian serum globulins, and bacterial polysaccharides.

Immunogenic compositions comprising GPVI polypeptides and peptides are encompassed by the invention. The immunogenic compositions can comprise carriers, adjuvants, and pharmaceutically acceptable compounds known in the art are provided in the series by P. Tijssen, *Practice and Theory of Enzyme Immunoassays*, 3rd Ed, 1987, Elsevier, New York.

It is understood that it may not be possible to generate antibodies against all GPVI peptides, since small peptides may not contain immunogenic epitopes. Nevertheless, such small peptides, such as from the extracellular doman and of at least three to five amino acids in length, may be useful in inhibiting the reaction between GPVI and its ligands, including collagen, are encompassed by the invention. Inhibitory peptides may, for example, be identified by recombinantly or synthetically synthesizing portions of the GPVI polypeptide and adding the purified sequences to any of the platelet assays described below. Once a portion of the molecule is determined to be inhibitory, successively smaller peptides from that region can be synthesized and applied to the assay to determine the minimum inhibitory region. Using this technique, it is possible to identify functional domains of GPVI, such as the collagen binding domain.

It is further understood that those antibodies which are able to bind GPVI polypeptides and peptides can be readily determined using conventional techniques, such as those in *Antibodies: A Laboratory Manual*, Harlow and Lane (eds.), Cold Spring Harbor Laboratory Press, 1988.

Equivalent DNA constructs that encode various additions or substitutions of amino acid residues or sequences, or deletions of terminal or internal residues or sequences are encompassed by the invention. For example, N-glycosylation sites in the GPVI polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

When used as an immunogen or therapeutic agent, GPVI polypeptides and peptides can be formulated into pharmaceutical compositions according to known methods. One or more GPVI polypeptides can be combined in admixture, either as the sole active material or with other known active materials, with pharmaceutically suitable diluents (e.g., Tris-HCl, acetate, phosphate, saline), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain GPVI polypeptides complexed with polyethylene glycol (PEG), metal ions, or incorporated into polymeric compounds such as polyacetic acid, polyglycolic acid, hydrogels, etc., or incorporated into liposomes (Dalecon et al., BBA 1302:241–48 (1996), microemulsions, micelles, unilamellar or multilamellar vesicles, erythrocyte ghosts or spheroblasts. Such compositions will influence the physical state, solubility, stability, rate of in vivo release, and rate of in vivo clearance of GPVI polypeptides.

Purified GPVI polypeptides according to the invention will facilitate the discovery of inhibitors of GPVI polypeptides. The use of a purified GPVI polypeptide in the screening of potential inhibitors thereof is important and can eliminate or reduce the possibility of interfering reactions with contaminants.

Generation of Anti-GPVI Antibodies

Anti-GPVI antibodies can be used for detecting the presence of GPVI polypeptides in a sample and may be used clinically to test for the presence of GPVI polypeptide in a patient. Further, the antibodies of the invention can be used therapeutically to bind to GPVI polypeptides and inhibit GPVI activities in vivo. In addition, such antibodies may be used to purify GPVI polypeptides; to identify the location and function of active sites on the GPVI molecule; and to purify cells expressing GPVI, including cells expressing recombinant GPVI and GPVI fusion proteins, by conventional methods including FACS and panning techniques, such as those described in *Antibodies: A Laboratory Manual*, Harlow and Lane (eds.), Cold Spring Harbor Laboratory Press, 1988; Merwe et al., *Eur J. Immunol.* 23:1373–1377, 1993; and U.S. Pat. No. 5,231,025 (Gralnick) and U.S. Pat. No. 5,468,468 (LaRochelle et al.) (Each of which is incorporated herein by reference.).

Within an aspect of the invention, GPVI polypeptides, and peptides based on the amino acid sequence of GPVI, can be utilized to prepare antibodies that specifically bind to GPVI polypeptides. The term "antibodies" is meant to include polyclonal antibodies, monoclonal antibodies, fragments thereof such as F(ab')2, and Fab fragments, as well as any recombinantly produced binding partners. Antibodies are defined to be specifically binding if they bind GPVI polypeptides with a $K_a$ of greater than or equal to about $10^7$ $M^{-1}$. Affinities of binding partners or antibodies can be readily determined using conventional techniques, for example those described by Scatchard et al., Ann. NY Acad. Sci., 51:660 (1949).

GPVI specific antibodies can be formulated into pharmaceutical compositions according to known methods. GPVI specific antibodies can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain GPVI polypeptides and or anti GPVI antibodies complexed.with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of GPVI specific antibodies.

Polyclonal Antibodies

Polyclonal antibodies can be readily generated from a variety of sources, for example, horses, cows, goats, sheep, dogs, chickens, rabbits, mice, or rats, using procedures that are well-known in the art. In general, purified GPVI polypeptides, or a peptide based on the amino acid sequence of GPVI polypeptides that is appropriately conjugated, is administered to the host animal typically through parenteral injection. The immunogenicity of GPVI polypeptides can be enhanced through the use of an adjuvant, for example, Freund's complete or incomplete adjuvant. Following booster immunizations, small samples of serum are collected and tested for reactivity to GPVI polypeptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,1110 and 4,486,530.

Monoclonal Antibodies

Monoclonal antibodies can be readily prepared using well-known procedures, see for example, the procedures described in U.S. Pat. Nos. RE 32,011, 4,902,614, 4,543, 439, and 4,411,993; Monoclonal Antibodies, Hybridomas: A New Dimension in Biological Analyses, Plenum Press, Kennett, McKearn, and Bechtol (eds.), 1980. Briefly, the host animals, such as mice are injected intraperitoneally at least once, and preferably at least twice at about 3 week intervals with isolated and purified GPVI polypeptides or conjugated GPVI polypeptides, optionally in the presence of adjuvant in the presence an adjuvant, such as RIBI adjuvant (RIBI Corp., Hamilton, Mont.). Mouse sera are then assayed by conventional dot blot technique or antibody capture (ABC) to determine which animals are best to fuse. Approximately two to three weeks later, the selected mice are given an intravenous boost of GPVI polypeptides or conjugated GPVI polypeptides. The mice are later sacrificed and spleen cells fused with commercially available myeloma cells, such as SP2/0, PU or Ag8.653 (ATCC), following established protocols. Briefly, myeloma cells are washed several times in serum-free media and fused to mouse spleen cells at a ratio of three spleen cells to one myeloma cell. The fusing agent is 50% PEG: 10% DMSO (Sigma). Fusion is plated out into twenty 96-well flat bottom plates (Corning) containing HAT supplemented DMEM media and allowed to grow for eight days. Supernatants from resultant hybridomas are collected and added to a 96-well plate for 60 minutes that is first coated with goat anti-mouse Ig. Following washes, $^{125}$I-GPVI recombinant or synthetic polypeptide or peptides are added to each well, incubated for 60 minutes at room temperature, and washed four times. Positive wells can be subsequently detected by autoradiography at −70° C. using Kodak X-Omat S film. Positive clones can be grown in bulk culture and supernatants are subsequently purified over a Protein A column (Pharmacia). It is understood of course that many techniques could be used to generate antibodies against GPVI polypeptides and peptides and that this embodiment in no way limits the scope of the invention.

The monoclonal antibodies of the invention can be produced using alternative techniques, such as those described by Alting-Mees et al., "Monoclonal Antibody Expression Libraries: A Rapid Alternative to Hybridomas", in Strategies in Molecular Biology 3:1–9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7.394 (1989).

Other types of "antibodies" can be produced using the information provided herein in conjunction with the state of knowledge in the art. For example, antiidiotype antibodies can be obtained by immunizing a host with an antigen comprising the antibody binding site of a purified monoclonal anti-GPVI antibody, and testing the resultant sera or monoclonal supernatent for activity as described in Knight et al., Mol. Immunol 32:1271–81 (1995). In addition, the invention comprises biosynthetic GPVI antibody binding sites, as described by Huston et al., (Proc. Natl. Acad. Sci. USA 85:5879 (1988); single-domain antibodies comprising isolated heavy chain variable domains, (Ward et al., Nature 341:544 (1989); and antibodies that have been engineered to contain elements of human antibodies that are capable of specifically binding GPVI polypeptides are also encompassed by the invention.

Anti-GPVI antibodies may also be generated using the phage display technology as described in the review by Ventor et al., Ann Rev. Immunol. 12:43355 (1994) and the references cited therein, all of which are incorporated herein by reference.

Hybrid Antibodies

Monoclonal antibodies are usually generated using the cells from mice, rats, or other small animals. The resultant antibodies find limited use in clinical studies because 1) many rodent antibody isotypes failed to activate human effector functions; 2) non-human antibodies are immunogenic in humans; and 3) immunogenicity can result in decreased antibody half-life and hypersensitivity. These difficulties may be avoided by replacing most, or all, of the structural portions of a monoclonal antibody with corresponding human antibody sequence. Consequently, a hybrid molecule is generated in which only the antigen-specific variable, or complementary determining region (CDR) is composed of non-human sequence. These humanized antibodies are thus particularly prefered for clinical use. See, for example, LoBuglio et al., Proc. Natl. Acad. Sci. USA 86:4220–24 (1989); Meredith et al., J. Nucl. Med. 33, 23–29 (1992); Salah et al., Hum. Antibod. Hybddomas 3:19–24 (1992); Knight et al., Mol. Immunol 32:1271–81 (1995); and Lockwood et al., Q. J. Med. 89:903–12, (1996).

Various strategies for designing these humanized antibodies are reviewed in Winter and Milstein, Nature 349:293–99 (1991); Harris, BCSTBS5 23(4):1035–38 (1995); S. Morrison and J. Schlom, in Important Advances in Oncology, J. B. Lippincott Co. (1990); L. Presta, "Humanized Monoclonal Antibodies," in Annual Reports in Medicinal Chemistry, Academic Press, (1994); and A. Lewis and J. Crowe, "Generation of Humanized Monoclonal Antibodies by 'Best Fit' Framework Selection and Recombinant Polymerase Chain Reaction " in Generation of Antibodies by Cell and Gene Immortalization. Year Immunol. 1993, vol 7, pp 110–118, (C. Terhorst, F. Malvasi, and A. Albertini (eds.) Basel, Karger, each of which is incorporated herein by reference.

Antibodies specific for GPVI will be selected and purified by Ig-specific adsorption, such as Protein A chromatography, or by affinity chromatography using immobilized GPVI peptide. The heavy and light chains will be dissociated by standard means, and the individual chains purified. A partial amino acid sequence of the individual chains will be determined and degenerate oligonucleotides generated against each according to the method of Lathe et al., J. Mol. Biol. 183:1–12 (1985). The DNA encoding these antibody chains will then be cloned from the producing cell by PCR or other standard methods and sequenced.

The antibody DNA and amino acid sequence will be analyzed according to standard methods in the art and compared with the known sequence of human heavy and light chains. Based on the sequence comparisons, the GPVI-specific antibody chains will be humanized by replacing portions of the non-human DNA with human-sequence, thus forming a chimeric antibody with specificity to GPVI. In one embodiment, the GPVI-specific antibody is humanized with human J1 and K constant regions using the expression vecotrs described by Sun et al., Proc. Natl. Acad. Sci. USA 84:214–218 (1987). Methods for the preparation of nonhuman-human hybrids are well known in the art and described in detail in, among other places, Knight et al., Mol. Immunol 32:1271–81 (1995); U.S. Pat. No. 5,705,154 (Dalie et al.); U.S. Pat. No. 5,693,322 (Creekmore et al.); U.S. Pat. No. 5,677,180 (Robinson et al.); U.S. Pat. No. 5,646,253 (Wallace et al.); U.S. Pat. No. 5,585,097 (Bolt et al.); U.S. Pat. No. 5,631,349 (Diamantstein et al.); and U.S. Pat. No. 5,580,774 (Beavers et al.) (each of which is incorporated herein by reference).

The generation of humanized antibodies is sometimes hampered by a loss of binding affinity, particularly when only a minimum of non-human sequence is retained. In order to maximize the production of high affinity antibodies, it is preferred that the chimeric antibody is designed using the methods of Queen et al., (U.S. Pat. No. 5,585,089) and Queen et al., Proc. Nat. Acad. Sci. USA, 86:10029–33 (1989), which are explicitly incorporated herein by reference.

Fab and F(ab)$_2$Fragments

Polyclonal, or more preferably, monoclonal antibodies, even more preferably, humanized monoclonal antibodies, specific for GPVI epitopes may be treated to remove the Fc antibody domain. Such treatments, usually by enzymatic digestion with pepsin or papain which result in bivalant, F(ab)$_2$ and monovalent, Fab fragments, respectively. These procedures are basically described in Tandon et al., Br. J. Haematol. 89:124–30 (1995) and *Antibodies: A Laboratory Manual*, Harlow and Lane (eds.), Cold Spring Harbor Laboratory Press, 1988; and U.S. Pat. No. 4,470,925 (Auditore-Hargreaves), and are well known in the art.

Intact GPVI-specific antibodies, Fab and F(ab)$_2$ fragments may be covalently coupled to drugs or carrier molecules. In addition, GPVI-specific antibodies may be cross-linked, directly, or through a suitable carrier molecule, to form multivalent complexes. In one embodiment, F(ab)$_2$ fragments are metabolically stabilized by covalent cross linking as described in Reno et al. (U.S. Pat. No. 5,506,342) (incorporated herein by reference).

Mono- and bi-valent antibodies immunoreactive with GPVI polypeptides, and in particular, monoclonal antibodies specific for GPVI epitopes will be tested for their ability to enhance or block platelet activation or ligand-dependent binding. Thrombus-promoting antibodies can be used as antihemorhagic agents and may be useful in limiting surgical or traumatic bleeding and enhancing wound healing. Antibodies which block platelet functions may be useful antithrombotic agents.

Screening for Factors which Interact with GPVI Functional Assay

Candidate GPVI agonists and antagonists may be screened for effects on adhesion and activation using various assays known in the art, for example, the assay for platelet adhesion inhibitor assay described in U.S. Pat. No. 5,686,571, the constant flow assay described in Moroi et al., Blood 88(6):2081–92 (1996), or in the plate assay described in Matsuno et al., British J. Haematology 92:960–967 (1996) and in Nakamura et al., J. Biol. Chem. 273(8):4338–44 (1998), (each of which is specifically incorporated herein by reference). In each case, candidate GPVI agonists or antagonists can be pre- or co-incubated with the reaction components in the presence and absence of $Mg^{2+}$. Incubation in the absence of $Mg^{2+}$ (e.g., in the divalent cation-free adhesion buffer described below) blocks the function of GPIa/IIa such that the remaining collagendependent activity is primarily mediated by the GPVI receptor. The remaining contribution from the GPIV receptor can be eliminated by using platelets from $NAK^a$-negative donors.

The Nakamura procedure can be used to measure platelet adhesion to immobilized monomeric and polymeric fibrillar collagen under static conditions. In addition, this assay can be used to measure platelet activation by monitoring the secretion of α-granules, dense granules, thromboxane $A_2$ generation, and collagen-induced ATP secretion. The Nakamura assay is described briefly below. However, one of skill in the art recognizes how to adjust the assay conditions in view of the particular agonist or antagonist to be tested.

Reagents—Acid-insoluble equine tendon fibrillar collagen (Chrono Par) is obtained from Chrono-Log Corp. (Broomall, Pa.). Acid-soluble rat tail type I collagen is purchased from Collaborative Biomedical Products Research (Bedford, Mass.). [2-$^{14}$C]Serotonin (5-hydroxytryptamine creatinine sulfate; 58 mCi/mmol) and $^{51}$Cr ($Na_2^{51}CrO_4$; 250 mCi/mg) are purchased from Amersham Corp. Prostaglandin $E_1$ is from Cayman Chemicals (Ann Arbor, Mich.). Enzyme immunoassay kits for thromboxane $B_2$ are from PerSeptive Diagnostic, Inc. Kits for PF4 and β-TG are obtained from Diagnostica Stago (France). Bovine serum albumin and other chemicals are purchased from Sigma.

Antibodies—Protein G affinity-purified mouse monoclonal antibody 6F1, directed against human platelet GPIa-IIa and recognizing the GPIa subunit, is generously provided by Dr. Barry S. Coller (Mount Sinai Medical School, New York). An unrelated mouse monoclonal antibody of the IgG$_1$ subclass (cone MOPC 21) is purchased from Sigma. A monospecific polyclonal antibody to human platelet GPIV (antibody 916) is raised in New Zealand White rabbits as described previously (Tandon et al., Blood 78:2089–13 (1991) ). A monospecific antibody against GPVI is purified from the plasma of a patient with idiopathic thrombocytopenic purpura who had developed an autoantibody against GPVI, i.e., the Okuma antibody. (Tandon et al., Br. J. Haematol. 89:124–30 (1995)). Fab fragments (Fabs) are prepared from the IgG fraction of the patient's plasma, from normal human plasma, and from the rabbit anti-GPIV serum by digestion with agarose-coupled papain utilizing an ImmunoPure Fab preparation kit (Pierce), principally according to the manufacturer's instructions but with slight modifications in the digestion temperature and the mode of shaking. In preliminary experiments using conditions suggested by the manufacturer, the resulting Fabs from the patient's IgG failed to block the aggregation of washed platelets by the intact IgG. In subsequent digestions, therefore, the IgG samples are digested at 35° C. in an oven with gentle rotation. The final product in each case is dialyzed extensively against HEPES-saline, pH 7.4. Fab fragments thus obtained retained their activity as judged by their ability to block aggregation of ished platelets induced by the corresponding intact IgG.

Platelet Preparation—Human blood is collected from healthy individuals who had not ingested any medication for at least 14 days prior to phlebotomy by the two-syringe method of venipuncture using a 19-gauge butterfly needle. Whole blood is collected directly into a syringe containing 3.8% sodium citrate as anticoagulant (9:1 whole blood/anticoagulant, v/v). Platelet-rich plasma is obtained by centrifugation at 150×g for 20 min. at room temperature. Washed platelets are prepared by the citrate wash method of Tandon et al., Blood 78:208913 (1991), with minor modifications. Briefly, citrate-washed platelets are suspended in Tyrode-HEPES buffer (136.7 mM NaCl, 5.5 mM glucose, 2.6 mM KCL, 13.8 mM, $NaHCO_3$, 1.0 mM $MgCl2.6H_2O$, 0.36 mM $NaH_2PO_4.H_2O$, 0.25% bovine serum albumin, pH 7.4) at a concentration of $2\times10^9$ platelets/ml. When required, platelets (1×10⁹) are labeled with $Na_2{}^{51}CrO_4$ (50 μCi/ml) for 1 h at room temperature followed by washing twice with citrate wash buffer containing 0.5% bovine serum albumin. To avoid platelet activation during washing and aggregation during adhesion assays, prostaglandin $E_1$ (250 ng/ml) is included in all buffers used to prepare washed platelets and in subsequent operations.

Adhesion Assay—Microtiter wells are coated with type I acid-insoluble equine tendon fibrillar collagen or with acid-soluble rat tail type I collagen maintained under acid conditions to ensure maintenance of monomer structure. Divalent cation-free adhesion buffer is made by replacing $Mg^{2-}$ (1 mM) in the Tyrode-HEPES buffer with μM EDTA. ⁵¹Cr-Labeled platelets are suspended in divalent cation-free adhesion buffer or in Tyrode-HEPES at a cell concentration of 3×10⁸/ml, and adhesion assays are carried out as described previously (Tandon et al., *Br. J. Haematol.* 89:124–30 (1995)). Briefly, ⁵¹Cr-Labeled platelets are incubated with a sample such as an antibody solution, for 30 minutes at room temperature prior to their addition to collagen-coated wells. Adhesion is carried out for 30 minutes at room temperature in the absence of $Mg^{++}$. Unattached platelets are removed by washing wells, the adhered platelets solubilized in SDS and counted in a beta counter to quantify adhesion.

Serotonin Release Reaction—For adhesion-induced secretion studies, washed platelets from a single donor are divided into two equal aliquots: one aliquot is labeled with ⁵¹Cr, while the other aliquot is labeled in parallel with [¹⁴C]serotonin. Washed platelets (1×10⁹ cells/ml) are incubated with ¹⁴C-labeled serotonin (0.1 μCi/ml, 1 μM) for 60 min. at room temperature. The unincorporated radioactivity is removed by washing the platelets twice with platelet wash buffer. Platelets are finally suspended in Tyrode-HEPES buffer containing $Mg^{2+}$ (1 mM) or EDTA (50 μM) and imipramine (1 μM) to stop the reuptake of released serotonin.

An aliquot (50 μl) of serotonin-loaded platelets is added to individual collagen-coated wells. At the desired times, adhesion is stopped by removing nonadhered platelets by washing each well six times by decantation using 200-μl aliquots of Tyrode-HEPES buffer containing 1 mM $MgCl_2$ or 50 μM EDTA (19). The adhered platelets are solubilized in DSD (2%) for 30 min., and their serotonin content is quantitated by counting the lysates in a β-counter (C). At the end of the incubation, an aliquot (50 μl) of unused platelet suspension is solubilized with an equal volume of SIDS (2%) and counted (T). An aliquot of the supernatant obtained from the unused platelet suspension is also counted to determine the background radioactivity (B). The adhesion rate (R=percentage of adhesion x-0.01) is quantitated in parallel experiments using ⁵¹Cr-labeled platelets. The adhesion-induced serotonin release is calculated by the following equation.

$$\text{Secretion }(\%) = \frac{(T-B) \times R - C}{(T-B) \times R} \times 100 \qquad (Eq.\ 1)$$

PF4 and β-TG Release—Levels of both PF4 (Platelet Factor 4) and β-TG (β-Thromboglobulin) are measured in the supernatants of the adhered platelets by commercially available kits based on enzyme-linked immunosorbent assay. At the desired times, nonadherent platelets are removed, and the wells are washed twice with wash buffer (200 μl). Suspensions of the nonadhered platelets and the two washes are combined and centrifuged at 6000×g for 2 min to sediment the platelets, and the supernatants are immediately frozen. At the same time, an aliquot (50 μl) of unused platelet suspension is also frozen. Subsequently, all samples are thawed on ice and made 1% with respect to Triton X-1 00 by adding an equal volume of chilled Triton X-100 (2%) in Tyrode-HEPES buffer. After 1 h on ice, samples are centrifuged at 15,000×g for 15 min at 4° C. to sediment Triton X-100-insoluble components. PF4 and β-TG levels are measured in the supernatants according to the manufacturer's instructions.

Thromboxane $A_2$ Generation—$TXA_2$ is measured as $TXB_2$, a stable metabolite of $TXA_2$, by a commercially available kit. At the desired times, unadhered platelets and suspending medium are transferred to ice-cold tubes and centrifuged 6000×g for 2 minutes to sediment platelets. Clear supernatants are kept frozen until used. Eicosanoids are extracted from the supernatants in ethyl acetate (27) prior to their quantitation by the immunosorbent assay kit. Briefly, the supernatants (100 μl) are acidified to a pH of 3–3.5 with formic acid (15 μl, 2.5%) and made 0.5 g/ml with respect to NaCl by the addition of 50 mg of solid NaCl to each tube, and eicosanoids are extracted twice with ethyl acetate (2.2 ml/extraction.) Organic phases from two extractions are combined and vacuum-dried. Samples are reconstituted in kit buffer for assay and processed further according to the manufacturer's instructions. In preliminary experiments, extraction efficiency is determined by lacing the supernatants with known amounts of tritium-labeled $TXB_2$ before extraction with ethyl acetate; 90–98% of the radioactivity is found in the organic phase.

Collagen-induced ATP-secretion—Collagen-induced ATP secretion is a measure of collagen-induced activation of platelets. Should there be any antibody against GPVI present in a sample, which could block a specific site on GPVI, the sample may also inhibit collagen-induced platelet secretion. These antibodies may be of clinical significance. In order to assay for such antibodies, a luciferase/luciferin assay system, which could detect platelet secretion in 96 well plates utilizing a small volume of platelets and luciferase/luciferin reagent, was developed. The assay is quick and can handle a large number of samples at a time. Briefly, blood is drawn directly into 3.8% trisodium citrate in a syringe (9:1 volume blood:citrate). Platelet-rich plasma (PRP) is prepared by centrifugation at 150×g for 20 minutes. PRP is mixed with 10 mM citric acid and spun at 800×g for 20 minutes to obtain a platelet pellet. Platelets are finally suspended in Tyrode-HEPES buffer (pH 7.4) supplemented with 0.5% BSA and 20 units/ml heparin. Platelet count is adjusted to 1×10⁸/ml. 50 ul of a sample suspected of containing antibodies against GPVI, such as culture supernatants collected from hybridoma cells, is added to the wells of a 96 well white plate. After the addition of 130 ul washed platelet suspension to each well, the plate is incubated for 10 minutes at 37° C. Platelet secretion is induced by injecting a diluted solution of collagen at a final concentration of 0.5 ug/ml. Plates are shaken on an ELISA plate shaker at a setting of 6 for 4 minutes. Collagen-induced ATP-secretion is quantified by adding 50 ul luciferase/luciferin reagent and the generated luminescence is detected for 1 second after a 1 second delay. 50 ul of culture medium from the same bottle is used as a negative control. Acetate buffer, which is used to dilute collagen stock solution, does not influence the basal luminescence. Prostaglandin E1 (PGE), which suppresses ATP secretion by 100%, is used as a positive control.

Platelet Aggregation Assay

A simple assay for detecting or determining antithrombotic activity is provided by the platelet aggregation assay, described in Knight et al., *Mol. Immunol* 32:1271–81 (1995). Although one of skill in the art recognizes that this assay may be adapted to test for GPVI agonist and antagonist activity of many compounds, it is particularly useful in testing the agonist and antagonist activity of polypeptides from the extracellular domain of GPVI and anti-GPVI antibodies. To test anti-GPVI antibodies, for example, ascites fluid, antibody, or control buffer (0.15 M Nacl, 0.1 M Tris-Hcl, 0.005% NaN$_3$, pH 7.4) is added to a cuvette containing platelet-rich plasma (prepared by centrifuging whole citrated human blood at 1875×g for 3.5 minutes) or 360 ul of washed platelet suspension. The mixture is incubated for 3 to 10 minutes prior to inducing aggregation. The cuvette is placed in a four channel optical aggregometer (Chronolog Corp. Havertown, Pa.) and aggregation is initiated with 0.5–1 ug/ml of collagen or 5 ng/ml of convulxin. Aggregation is monitored for at least 5 minutes turbidimetrically as the increase in light transmission.

Ex Vivo Assay

The antagonistic, agonistic, or antithrombotic activities of candidate compounds, including GPVI specific antibodies, antibody fragments, GPVI polypeptides, including soluble polypeptides, can be further assayed using the systems developed by Diaz-Ricart and co-workers (*Arteriosclerosis, Thromb. Vasc. Biol.* 16:883–888 (1996)), incorporated by reference. This assay determines the effect of candidate compounds on platelets under flow conditions using deendotheliailized rabbit aorta and human endothelial cell matrices.

In Vivo Assay

Once candidate GPVI-inhibitory compounds are identified, the in vivo activity of these antagonists can be assayed using standard models of platelet function as described in Coller and Scudder, *Blood* 66:1456–59 (1985); Coller et al., *Blood* 68:783–86 (1986); Coller et al., *Circulation* 80:1766–74 (1989); Colleret at al., *Ann. Intern. Med.* 109: 635–38 (1988); Gold et al., *Circulation* 77, 670–77 (1988); and Mickelson et al., *J. Molec. Cell Cardiol.* 21:393–405 (1989).

Production of Soluble Recombinant (sr)GPVI

Analyses of the amino acid sequence of GPVI suggests that amino acids 1–23 encode a putative signal sequence, followed by an an extracellular domain spanning about amino acids 24 through 269, and a transmembrane and intracellular domain beginning at about amino acid 270. To express a soluble form of GPVI, the extracellular domain was cloned, expressed, and purified using the yeast expression system, EasySelect™ Pichia Expression Kit (Invitrogen), essentially as directed by the supplier.

Specifically, total RNA was isolated from human platelets and nucleotides 1 to 1015 of the GPVI cDNA sequence of SEQ ID NO:4 was PCR amplified using the forward PCR primer (5'-gagctcagg*acagggctgaggaacc*-3') (SEQ ID NO: 6) and reverse PCR primer (5'-gtgccctca*tgagtcgcctcccatg*-3) (SEQ ID NO: 7) (underlined portions represent sequences hybridizing to the GPVI sequence). The 1 kb fragment was cloned into the pTarget vector obtained from Promega. This new vector, pTargetGPVI, was used to PCR amplify the sequences encoding for the extracellular domain of GPVI. The forward primer (5'-ata*ggcccagccggcc*tcagagtggaccgc-3') (SEQ ID NO: 8) and the reverse primer (5'-tgttc*tagac*cgttgcccttggtgtagtac-3') (SEQ ID NO: 9) used for amplification of the external domain were synthesized to contained SfiI and XbaI sites (underlined), respectively, for cloning into the yeast expression vector pPZICZα (Invitrogen). Using these primers, nucleotide sequences 78 to 824 of SEQ ID NO:4 are amplified and are flagged by SfiI and XbaI sites. This 750 bp fragment of GPVI DNA was inserted into the the SfiI and XbaI sites of the vector as shown in FIG. 4. The protein produced from the new vector, pPICZGPVI, is depicted in FIG. 5. The underlined portion represents the external domain of GPVI, which is preceded by the a factor of yeast. The external domain is also linked to the myc epitope (in italics and bold) and a His tag (six histidines).

Figure 6:
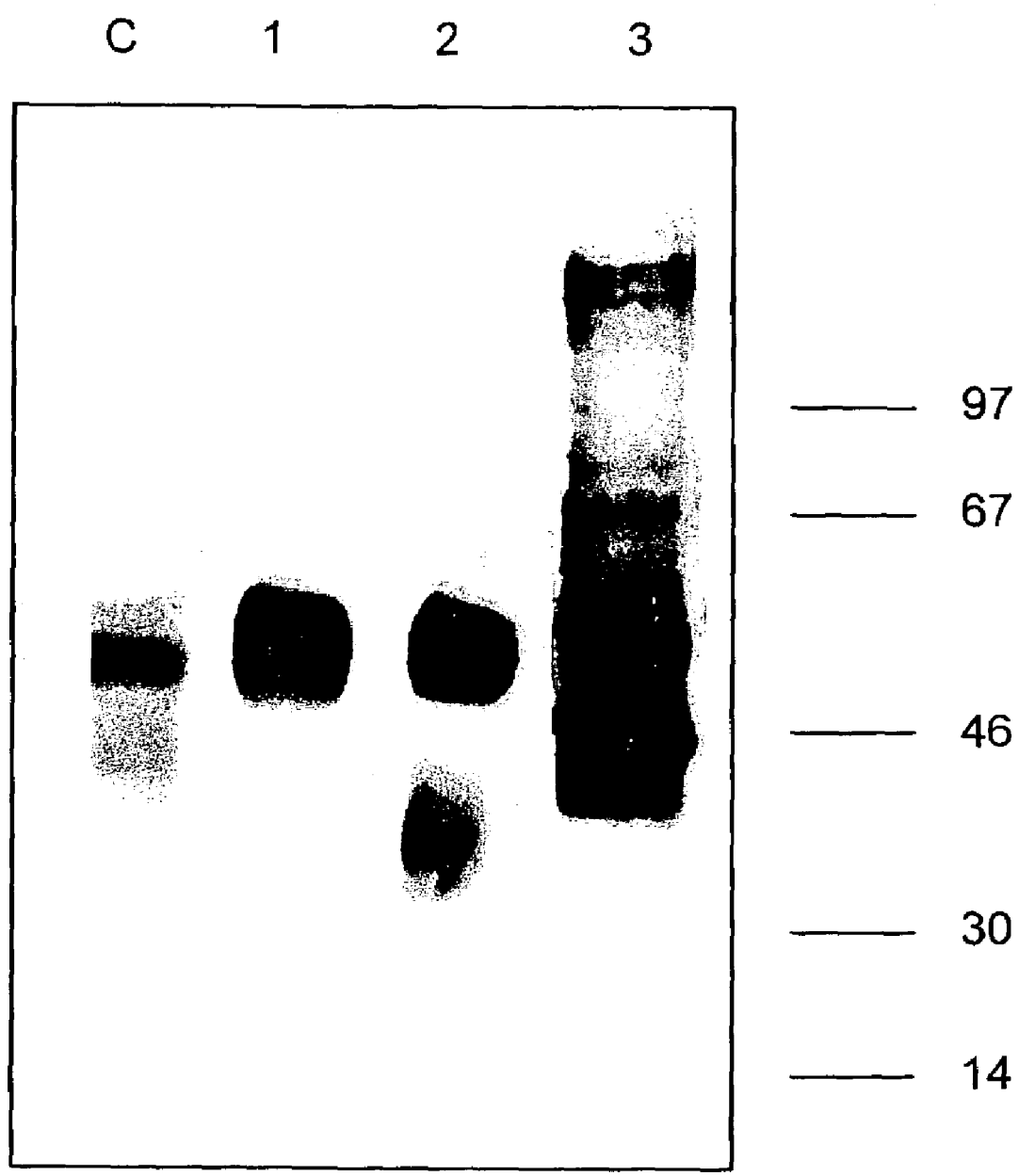
FIG. 6 illustrates recombinant GPVI electrophoresed on an 8% SDS-PAGE gel after purification from the yeast expression system.

For production of soluble recombinant GPVI, the vector, pPICZGPVI, was transformed into yeast and yeast was grown in volumes ranging from 200 to 1000 ml. The supernatant enriched with the engineered vector was collected for the purification of the corresponding products. The secreted products, bearing a poly-histidine tag, were adsorbed onto a Ni-Sepharose matrix. After extensive washing, the protein bound to immobilized nickel through the poly-histidine domain was released by a gradient of imidazole. Eluted protein was dialyzed against PBS to remove imidazole. Recombinant GPVI (srGPVI) was electrophoresed on an 8% SDS-PAGE gel and transferred to nitrocellulose to confirm its identity (FIG. 6). Recombinant GPVI reacted in a Western blot, as expected, with monoclonal anti-myc antibody (lane 2) confirming that it had both the myc and poly-His tags. In addition, recombinant GPVI reacted with covulxin (lane 1), a ligand for GPVI. Recombinant GPVI was further confirmed by staining the protein with Coomassie Brilliant Blue (land C) and Western blotting with an anti-GPVI antibody obtained from human serum (lane 3).

srGPVI produced from this system can be used in assays such as ELISAs to screen for antibodies against GPVI. Additionally, srGPVI can also be used to raise antibodies against srGPVI.

Collagen Binding of the Extracellular Domain of GPVI

Figure 7:
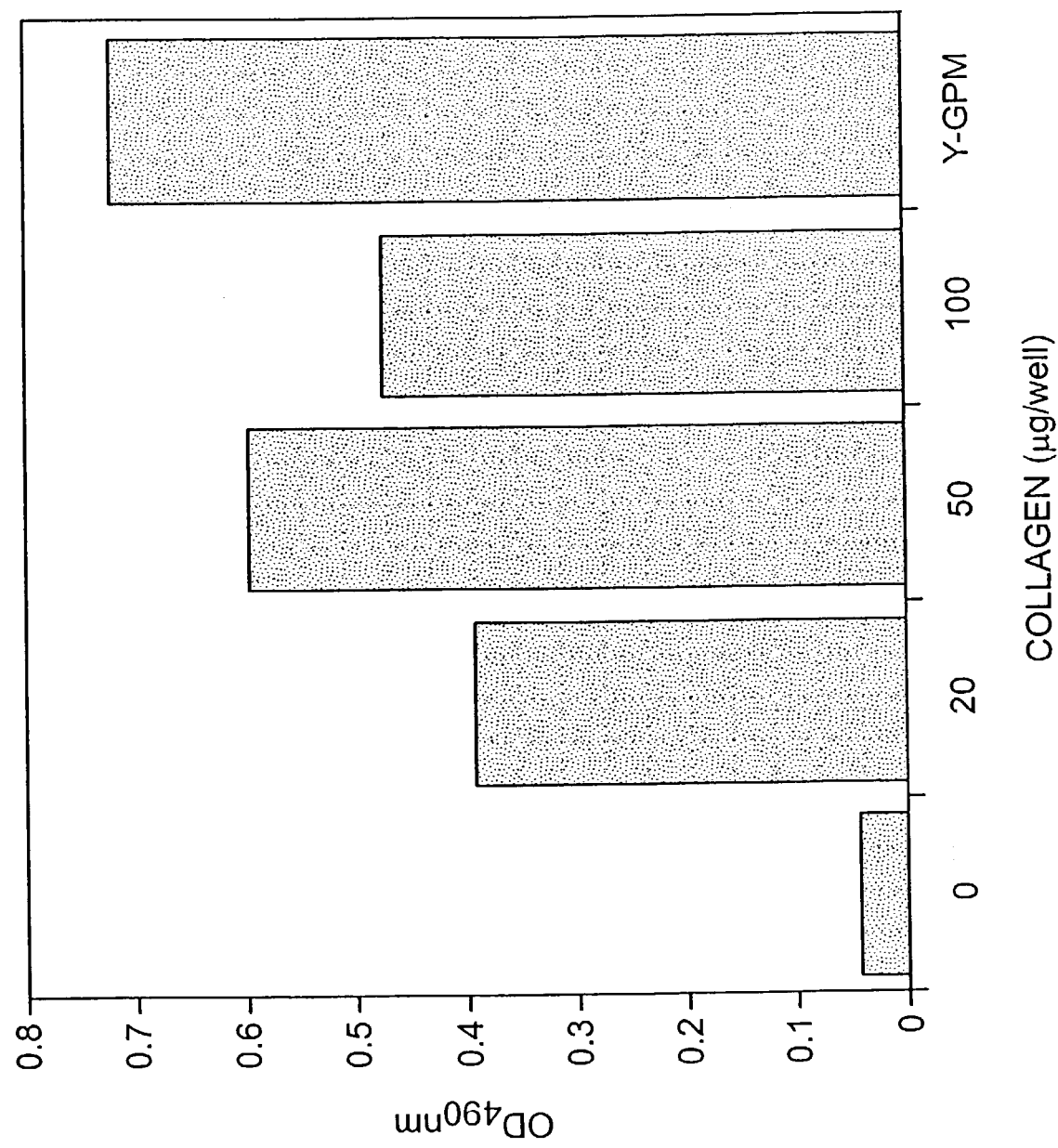
FIG. 7 illustrates collagen binding of recombinantly-produced GPVI.

Collagen binding of the extracellular domain of GPVI was first comfirmed and illustrated in FIG. 7. Briefly, equine tendon acid soluble collagen (Chlonolog Corp, Pa.) was diluted in 5 mM acetic acid. 50 ul aliquots containing 0, 20, 50, or 100 ug of collagen were added to microtiter wells and incubated overnight at 4° C. The wells were blocked with 5% milk in TBS. 50 ul of culture supernatant of yeast containing recombinant GPVI was added to each well and incubated for 60 min at room temperature. Unbound GPVI was removed by washing five times with TBS. GPVI was incubated for two hours with an anti-myc antibody which recognizes the myc-tag on the recombinant protein. Following the removal of free antibody, the bound anti-myc antibody was detected by a combination of HRP-labeled goat anti mouse IgG and a color substrate O-phenylendiamine. Wells coated with recombinant GPVI was used as a positive control. FIG. 7 shows that soluble recombinant GPVI is capable of binding to collagen.

The Extracellular Domain of GPVI has Potent Anti-Thrombotic Activity

Figure 8:
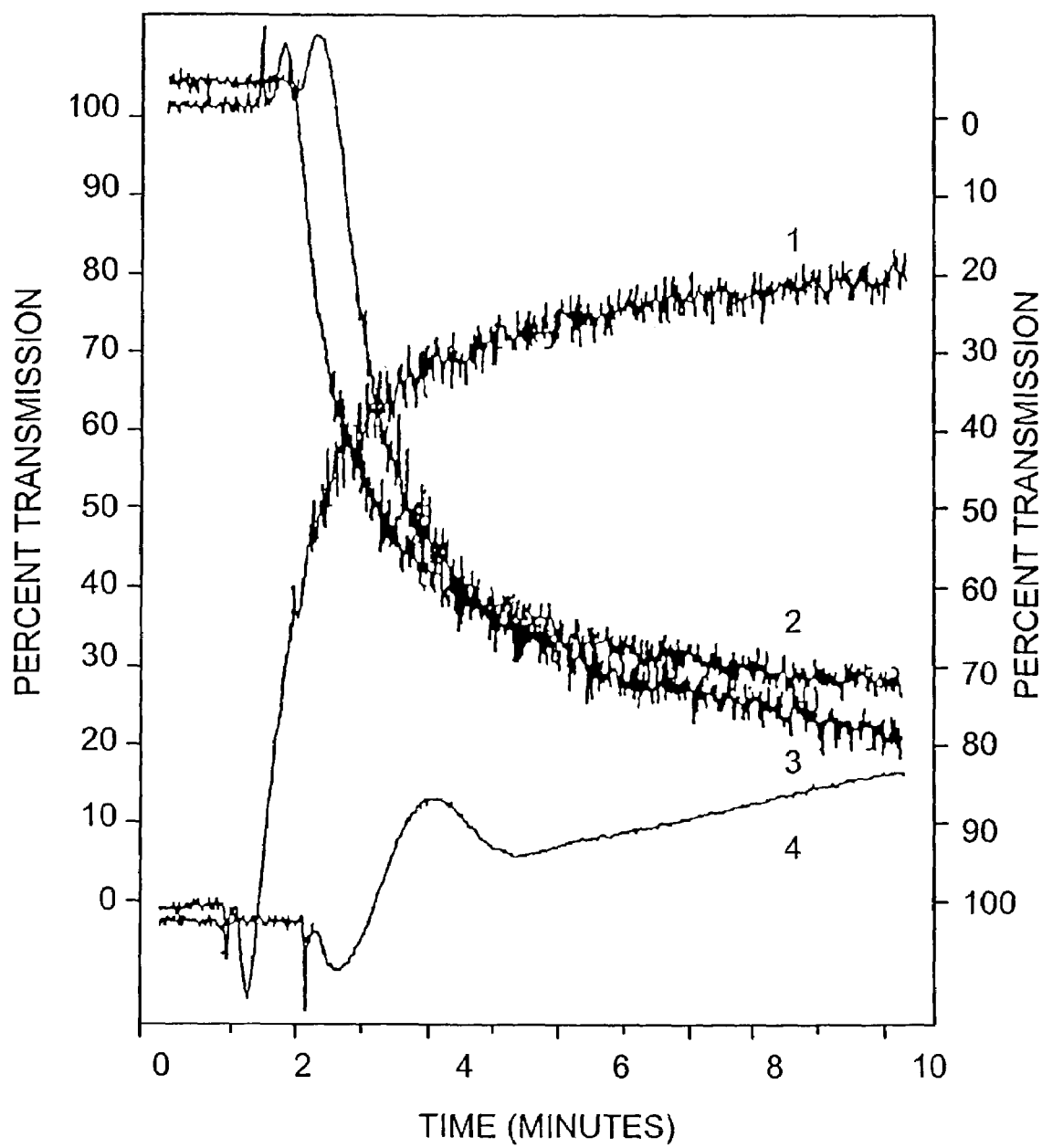
FIG. 8 illustrates the inhibition of convulxin-induced platelet aggregation by recombinant GPVI.

The soluble recombinant (sr)GPVI was tested for anti-thrombotic acitivity by detecting inhibition of convulxin-induced and collagen-induced platelet aggregation according to the Plate Aggregation Assay described above. Briefly, to assay for convulxin-induced platelet aggregation, plasma rich platelets were incubated with 0, 3, 6, or 12 ug per ml of recombinant GPVI for 3 to 4 minutes prior to the addition of 5 ng/ml of convulxin. Aggregation was followed for at least 6 minutes. Reduction in light transmission reflects an inhibition in platelet aggregation. FIG. 8 illustrates the dose-dependent inhibition of convulxin-induced platelet aggregation. Curves 1 (no recombinant GVPI) and 4 (12 ug of recombinant GPVI) are plotted from 0–100% transmission whereas curves 2 (3 ug of recombinant GPVI) and 3 (6 ug of recombinant GPVI) are plotted from 100–0% transmission. A comparison of curves 1 and 4 demonstrates that recombinant GPVI competes with platelet GPVI, reducing the effective concentration of convulxin to react with platelet GPVI and to induce aggregation.

Figure 9:
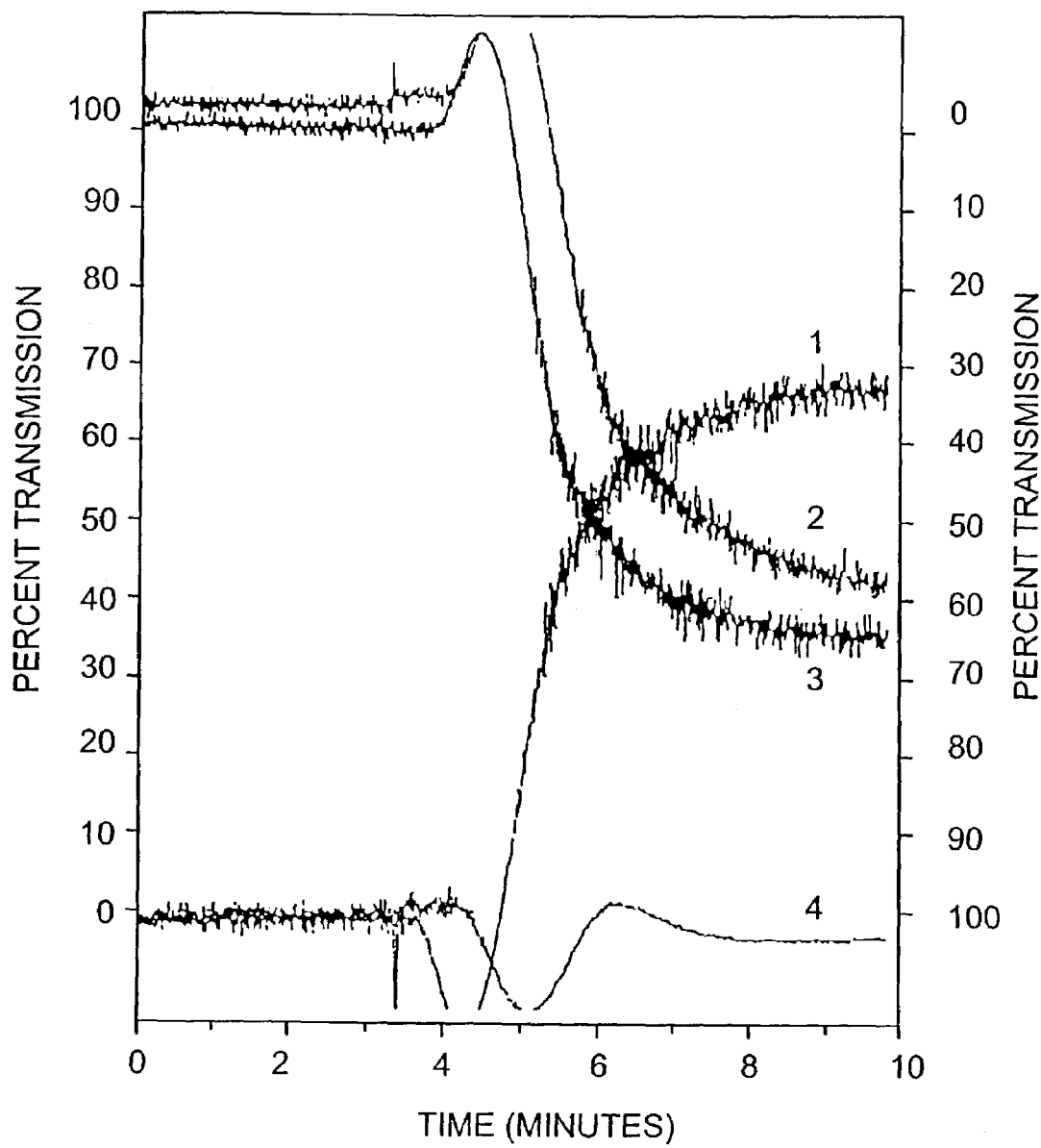
FIG. 9 illustrates the inhibition of collagen-induced platelet aggregation by recombinant GPVI.

Collagen-induced aggregation was similarly assayed, except that 0, 6, 12, and 24 ug per ml of recombinant GPVI was incubated with plasma rich platelets and 0.5ug/ml of collagen was added to induce aggregation. FIG. 9 illustrates the dose-dependent inhibition of collagen-induced platelet aggregation by recombinant GPVI. Again, curves 1 (no recombinant GVPI) and 4 (24 ug of recombinant GPVI) are plotted from 0–100% transmission whereas curves 2 (6 ug of recombinant GPVI) and 3 (12 ug of recombinant GPVI) are plotted from 100–0% transmission. Similar to FIG. 8, recombinant GPVI inhibits collagen-induced platelet aggregation at higher doses (12 ug of recombinant GPVI).

The extracellular portion GPVI protein may be used therapeutically to attenuate platelet activation and aggregation, and to treat thrombotic, and other vascular diseases. Consequently, these polypeptides can be incorporated into medicaments or pharmaceutical compositions for the treatment of vascular ailments and conditions. The purification of GPVI directly from platelets, however, involves the use of detergents to solubilize the cellular membranes. These detergents may be difficult to remove using standard purification methods. Consequently, where a detergent-free polypeptide preparation is prefered, it is highly desirable to produce the GPVI polypeptides synthetically or recombinantly, such that the use of detergents may be avoided.

In addition to the full-length extracellular domain, variants, including recombinant, proteolytic, or synthetic sub-fragments of this region may also exhibit anti-thrombotic activity. As is appreciated by one of ordinary skill in the art, such variants may be easily produced and tested for activity using standard anti-thrombotic assays. These biologically-active variants may be more amenable to large-scale synthesis and enhance the cost-effectiveness of producing such anti-thrombotic compounds.

Generation of Monoclonal Antibodies Against Platelet GPVI

Antibodies raised against GPVI purified from platelets may be advantageous for therapeutic purposes. For example, recombinantly-produced proteins may not possess the same three-dimensional folding, glycosylation, and post-translational modifications as the naturally-occurring protein. Consequently, antibodies raised against recombinant GPVI may lack some of the bioactive properties associated with those derived from naturally-occurring GPVI, or even fail to recognize the GPVI in its native state.

200 μg of the native GPVI product purified as described above, but obtained prior to convulxin affinity chromatography (see section on purification of GPVI from human platelets), was injected four times into BALB/c mice at an interval of seven days. Three days after the last injection, lymphocytes were harvested from the spleen. Lymphocytes ($5 \times 10^7$) were fused with SP2/0 cells ($2.5 \times 10^7$) in the presence of PEG 3700 (Sigma) using the standard protocol outlined above. The fused cells were initially cultured in 96 well culture dishes at a cell density of $5 \times 10^5$ cells/well.

After five days of culture, production of monoclonal antibodies in the culture supernatants was examined by the ELISA method using recombinant GPVI produced from pPICZGPVI (srGPVI) and platelets immobilized on microtiter wells to test for reactivity to native GPVI. Culture supernatants were also examined for inhibitory effect on collagen-induced platelet aggregation and ATP-secretion. Platelet aggregation assays were performed in a four channel optical aggregometer using either platelet rich plasma or washed platelet suspensions as described above. Collagen-induced ATP secretion was measured in a 96 well luminometer. In addition to the above tests, the presence of anti-GPVI antibodies in the supernatants was also confirmed by Western-blot analysis using lysate from unlabeled platelets. Forty one wells reacted positively in both ELISA tests using recombinant and platelets. Furthermore, they also reacted positively in the Western blot analysis against recombinant GPVI and inhibited collagen-induced platelet functions discussed above. Limiting dilution was performed on these cells. The diluted cultures were further analyzed for collagen-induced ATP secretion and the results are depicted in the second column of Table 2. Some cultures were also tested for reactivity against recombinant GPVI (srGPVI) by Western (FIG. 10) blot and/or for their inhibitory effect on platelet aggregation (FIG. 11). The results of these studies are summarized in Table 2.

TABLE 2

| Culture # | ATP Secretion (% secretion) | Western-blot (srGPVI) | Aggregation | Activation-dependent platelet binding |
|---|---|---|---|---|
| OPM1 | Inhibitory[a] (58.6) | ND[b] | Lag[c] | ND |
| OPM2 | Inhibitory (79.3) | Positive | +/− inhibition[d] | ND |
| OPM3 | Inhibitory (73.8) | Positive | Inhibitory (lag) | ND |
| OPM4 | Inhibitory (85.5) | Positive | No inhibition | ND |
| OPM5 | Inhibitory (80)* | ND | Inhibitory (lag) | ND |
| OPM6 | Inhibitory (78.5) | ND | Inhibitory (lag) | ND |
| OPM7 | Inhibitory (83.2) | ND | +/− inhibition | ND |
| OPM8 | Inhibitory (80.3)* | Negative | No inhibition | ND |
| OPM9 | Inhibitory (67.6) | ND | No inhibition | ND |
| OPM10 | Inhibitory (60.1)* | Positive | Inhibitory | ND |
| OPM11 | No inhibition (101.5)* | ND | Inhibitory | ND |
| OPM12 | No inhibition (124.6) | Negative | No inhibition | ND |

TABLE 2-continued

| Culture # | ATP Secretion (% secretion) | Western-blot (srGPVI) | Aggregation | Activation-dependent platelet binding |
|---|---|---|---|---|
| OPM13 | Inhibitory (86.6) | Negative | Inhibitory | ND |
| OPM14 | No inhibition (106.6)* | Negative | Inhibition | ND |
| OPM15 | No inhibition (120.5)* | Positive | No inhibition | Yes |
| OPM16 | Inhibitory (83.9)* | Positive | Inhibition | ND |
| OPM17 | Inhibitory (88.5) | ND | ND | ND |
| OPM18 | Inhibitory (85.4) | Positive | ND | ND |
| OPM19 | Inhibitory (85.4)* | Positive | +/− inhibition | ND |
| OPM20 | Inhibitory (83.5) | Positive | +/− inhibition | ND |
| OPM21 | Inhibitory (80.9) | Positive | Inhibitory | ND |
| OPM22 | No inhibition (94.3) | Positive | Inhibitory | ND |
| OPM23 | No inhibition (93.4) | Positive | Inhibitory | ND |
| OPM24 | Inhibitory (81.9) | Positve | No inhibition | ND |
| OPM25 | No inhibition (98.8) | ND | Inhibitory | ND |
| OPM26 | Inhibitory (83.1) | ND | ND | ND |
| OPM27 | Inhibitory (89.6) | ND | Inhibitory | ND |
| OPM28 | Inhibitory (80.2) | ND | ND | ND |
| OPM29 | Inhibitory (73.6) | ND | ND | ND |
| OPM30 | Inhibitory (84.9) | ND | ND | ND |
| OPM31 | Inhibitory (86) | ND | ND | ND |
| OPM32 | Inhibitory (63.7) | ND | ND | ND |
| OPM33 | No inhibition (92) | ND | ND | ND |
| OPM34 | No inhibition (98.2) | ND | ND | ND |
| OPM35 | No inhibition (100.4) | Positive | ND | ND |
| OPM36 | Inhibitory (78.9) | ND | ND | ND |
| OPM37 | Inhibitory (85.6) | ND | ND | ND |
| OPM38 | Inhibitory (78.5) | ND | ND | ND |
| OPM39 | Inhibitory (71.5) | ND | ND | ND |
| OPM40 | Inhibitory (74.6) | ND | ND | ND |
| OPM41 | Inhibitory (76.5) | ND | ND | ND |
| CONTROL | No inhibition (100) | | | |

[a]Inhibitory effect is defined as ATP secretion of less than 90%.
[b]Not determined.
[c]Some lag time in observed effect.
[d]Weak inhibition.
*These cultures were also tested for their effect on collagen-induced platelet aggregation and results are shown in FIG. 11.

Figure 10:
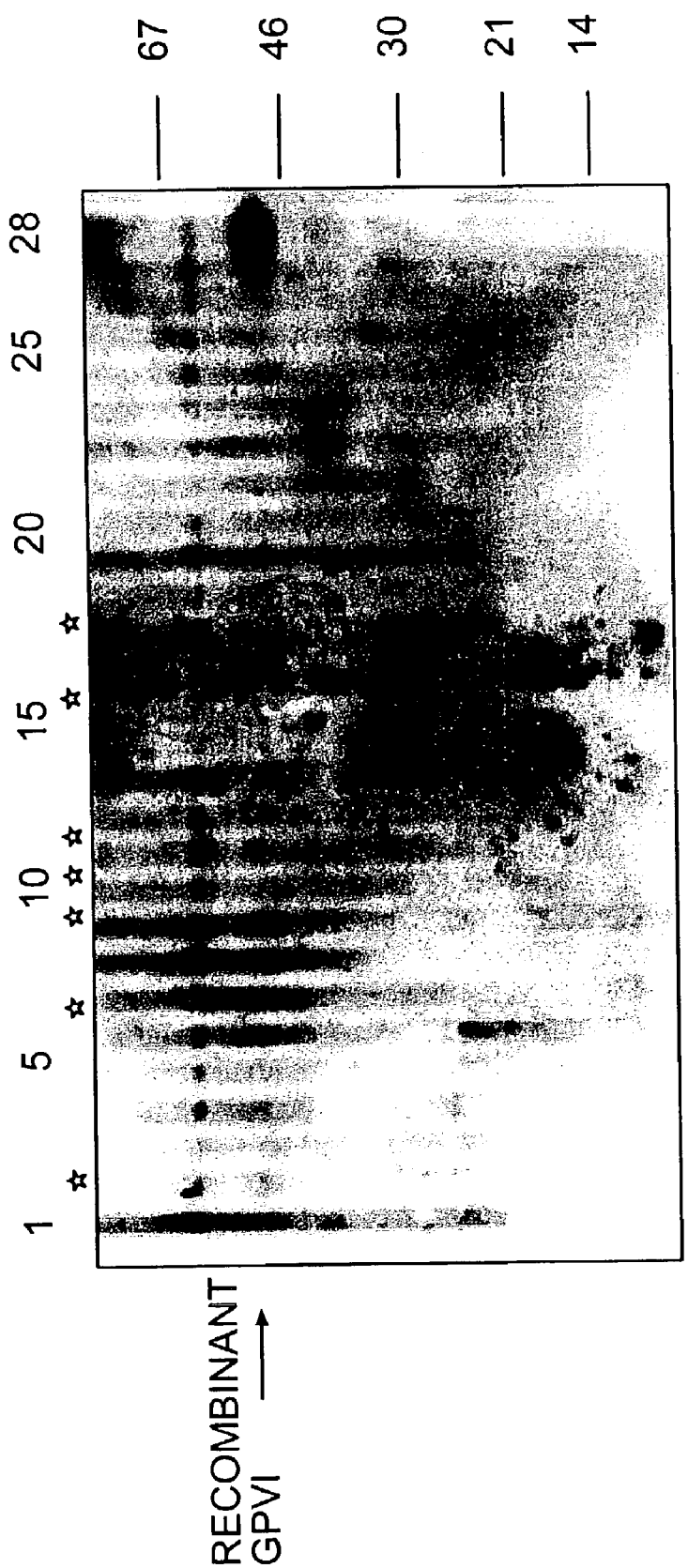
FIG. 10 illustrates reactivity of cultures of monoclonal antibodies to recombinant GPVI in a Western blot analysis.
Figure 11:
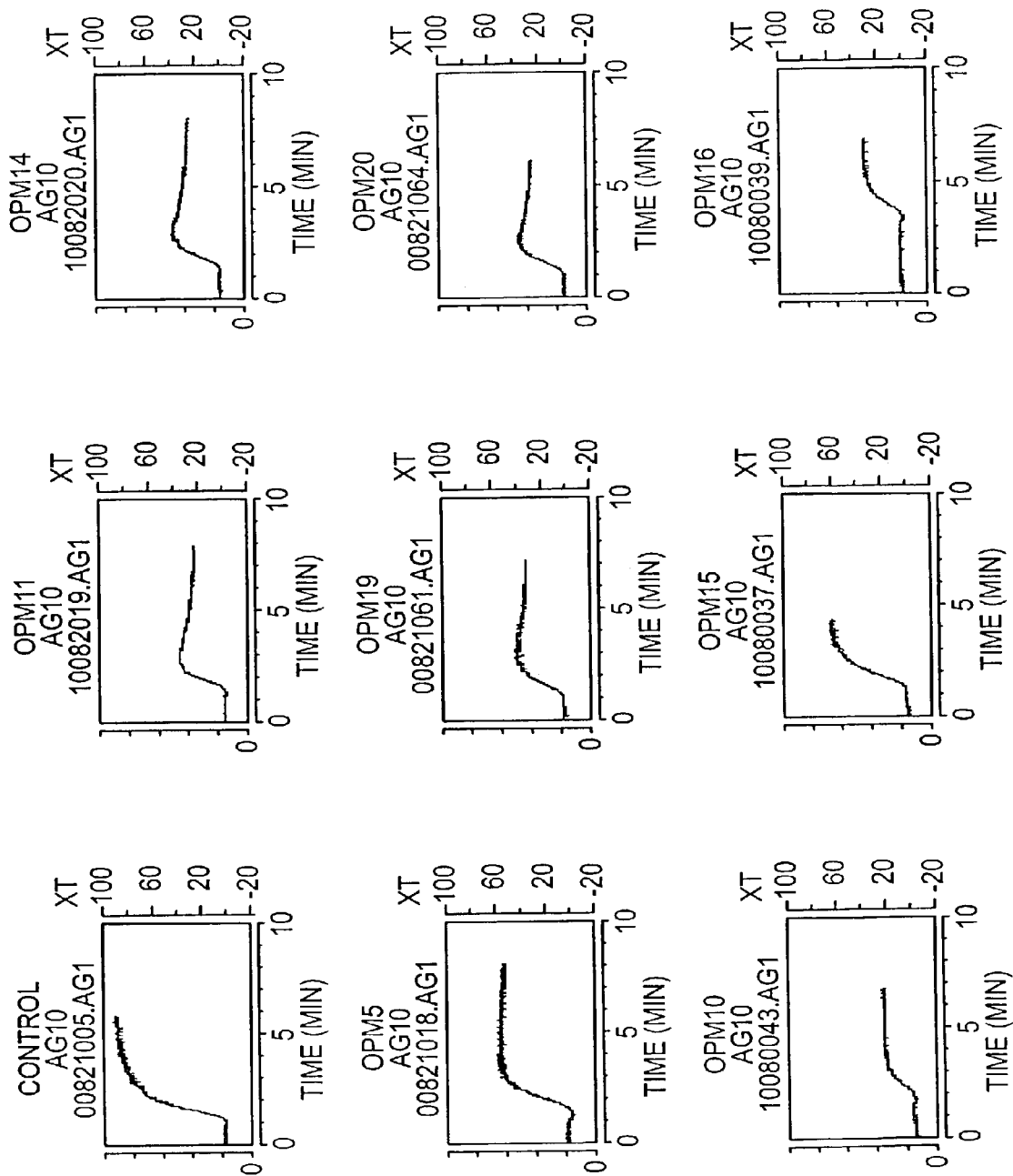
FIG. 11 illustrates inhibitory effects on collagen-induced platelet aggregation by monoclonal antibody cultures.

Cultures OPM 10, OPM 20, OPM 19, OPM 21, OPM 22, OPM 12, and OPM 23 showed significant reactivity against srGPVI in Western blot analysis (FIG. 10, lanes 2, 7, 9, 10, 11, 15, and 17, respectively). The results of collagen-induced platelet aggregation analyses are depicted in FIG. 11, where platelet aggregation results in an increase in light transmission. Cultures OPM 10, OPM 16, OPM 11, OPM 14, OPM 19, OPM 20, and OPM 5 all showed inhibition of platelet aggregation, whereas culture OPM 15 showed no effect on platelet aggregation.

Many of the cultures, for example OPM 3, OPM 10, and OPM 21, displayed inhibition in both ATP secretion and in platelet aggregation. Some cultures, such as OPM 8 and OPM 13, inhibited both ATP secretion and platelet aggregation but were negative in Western blots against recombinant GPVI. This suggests that these monoclonal antibodies may preferentially bind to native GPVI. Alternatively, the antibodies in OPM 8 and OPM 13 may be too dilute to give a signal by Western blot, yet exhibit substantial anti-thrombotic activity, even at very low concentrations.

Supernatants from OPM 4 and OPM 24, for example, inhibited ATP secretion but not platelet aggregation. Conversely, OPM 11, OPM 14, OPM 22, OPM 23, and OPM 25 showed no inhibition of ATP secretion but did inhibit platelet aggregation. The monoclonal antibodies in these supernatants may bind epitopes essential for either signal transduction leading to ATP secretion or platelet aggregation.

Some of the cultures were further analyzed by ELISA for their ability to bind to activated platelets versus unstimulated (resting) platelets. To test for activation-dependent binding to platelets, platelets were separated from platelet rich plasma (PRP) and washed twice by the standard method. Washed platelets ($1.5 \times 10^7$) were coated onto 96 wells of an ELISA plate (Dynatech Laboratories) by centrifugation (Beckman J-6B) at 2000 rpm for 15 minutes. Platelets were fixed with 1% paraformaldehyde for 30 min. After washing twice with PBS, the surface of the plate was blocked overnight with PBS containing 5% non-fat dry milk (NFDM). The plate was kept at 4° C. until used. To test for activation-dependent binding to platelets, the coated platelets were stimulated with 0.1 unit/ml thrombin 10 min before fixation with 1% paraformaldehyde.

Culture supernatant (50 ul) was then added to the platelet-coated wells and incubated overnight at 4° C. After washing 3 times with PBS, peroxidase-labeled goat anti-mouse Ig (1/2000 dilution) was added to the wells and incubated further for 120 min at room temperature. After washing three times, color due to peroxidase reaction was developed by the addition of 50 ul of substrate, O-phenylendiamine solution (Zymed). The color reaction was terminated by the addition of equal volume of 2N $H_2SO_4$ and the color was read at 490 nm in an ELISA plate reader.

Of particular interest was culture OPM 15. Culture OPM 15 had no effect on collagen-induced ATP secretion or platelet aggregation but showed activation-dependent binding to platelets. This suggests that this antibody recognizes an epitope specific for activated platelets and that it may be effective in inhibiting thrombotic activities that occur post-activation.

Methods of Treatment

The instant invention comprises methods of inhibiting thrombosis, for example, by inhibiting platelet aggregation or platelet activation, comprising contacting activated or resting platelets with either 1) antibodies directed against GPVI, or 2) with polypeptides encoded by the nucleotides of SEQ ID NO: 4, which include the full-length GPVI protein, in particular, any polypeptide from the extracellular domain of GPVI (approximately amino acids 24 through 269), including variants and derivatives thereof. Without limitation to any particular theory of the invention, it is currently believed that the extracellular domain of GPVI inhibits platelet activation by binding to collagen. Consequently, the latter embodiment encompasses the indirect contact of GPVI with platelets. The inhibitory polypeptide may comprise the entire extracellular domain, or any smaller peptide having at least about 6, 8, 10, 15, 20, 30, 40, 50, 100, or 244, contiguous amino acids of the extracellular domain, or any length of contiguous GPVI amino acids subsumed within these ranges. Inhibitory polypeptides may be soluble, include polypeptide aggregates, mixtures or combinations of polypeptides, and comprise naturally-occurring, synthetic and recombinantly-derived amino acid sequences.

The invention further relates to the treatment of a patient, hereby defined as any person or non-human animal in need of anti-thrombotic treatment to reduce the incidence or likelihood of thrombosis, or platelet aggregation, or platelet activation, or to any subject for whom treatment may be beneficial for the treatment of vascular disease, including humans and non-human animals. Such non-human animals to be treated include all domesticated and feral vertebrates including, but not limited to: mice, rats, rabbits, fish, birds, hamsters, dogs, cats, swine, sheep, horses, cattle, and non-human primates.

The treatment of a patient comprises the administration of a pharmaceutically effective amount of an anti-GPVI antibody or GPVI polypeptide-containing composition of the invention. One of ordinary skill in the art may empirically determine the optimum dosage and dosage schedule for administering these compositions. Nevertheless, a pharmaceutically effective amount is that amount which provides a measurable anti-thrombotic effect, for example, a reduction in the incidence, degree, or likelihood of thrombosis, platelet aggregation, or platelet stimulation as measured in vivo or in vitro, or provides a measurable decrease in the likelihood, incidence, or degree of 1) vascular disease; or 2) clot or emboli formation; or 3) ischemic events in a patient.

The compositions of the invention may be administered by any method familiar to those of ordinary skill in the art, for example, intravenous administration by bolus injection, continuous, or intermittent infusion. In alternative embodiments, the compositions may be administered intraperitoneally, intracorporeally, intra-articularly, intraventricularly, intrathecally, intramuscularly, subcutaneously, topically, tonsillarly, mucosally, intranasally, transdermally, intravaginally, orally, or by inhalation.

The specification is most thoroughly understood in light of the teachings of the references cited within the specification, which are all hereby incorporated by reference in their entirety. The embodiments within the specification provide an illustration of embodiments of the invention and should not be construed to limit the scope of the invention. The skilled artisan recognizes many other embodiments are encompassed by the claimed invention.

It is intended that the specification and examples be considered as exemplary only, with a true scope and spirit of the invention being indicated by the following claims.

We claim:

1. A monoclonal antibody which specifically binds with peptide KPSLQALPSSLVPLEK (SEQ ID NO: 18).

2. A monoclonal antibody which specifically binds to SEQ ID NO: 5, wherein the antibody inhibits collagen-induced ATP secretion and human platelet aggregation, wherein the antibody is bivalent.

3. A monoclonal antibody which specifically binds to SEQ ID NO: 5, wherein the antibody inhibits human platelet aggregation but does not inhibit collagen-induced ATP secretion, wherein the antibody is bivalent.

* * * * *

SEQUENCE LISTING

```
<160> NUMBER OF SEQ ID NOS: 37
<210> SEQ ID NO 1
<211> LENGTH: 240
<212> TYPE: DNA
<213> ORGANISM: Homo sapiens

<400> SEQUENCE: 1
acagggctga ggaaccatgt ctccatcccc gaccgccctc ttctgtcttg ggctgtgtcy      60
ggggcgtgtg ccagcgcaga gtggaccgct ccccaagccc tccctccagg ctctgcccag    120
ctccctggtg cccctggaga agccagtgac cctccggtgc cagggacctc cgggcgtgga    180
cctgtaccgc ctggagaagc tgagttccag caggtaccac gatcaggccg tcctcttcat    240

<210> SEQ ID NO 2
<211> LENGTH: 74
<212> TYPE: PRT
<213> ORGANISM: Homo sapiens

<400> SEQUENCE: 2

Met Ser Pro Ser Pro Thr Ala Leu Phe Cys Leu Gly Leu Cys Leu Gly
  1               5                  10                  15

Arg Val Pro Ala Gln Ser Gly Pro Leu Pro Lys Pro Ser Leu Gln Ala
                 20                  25                  30

Leu Pro Ser Ser Leu Val Pro Leu Glu Lys Pro Val Thr Leu Arg Cys
             35                  40                  45
```

Gln Gly Pro Pro Gly Val Asp Leu Tyr Arg Leu Glu Lys Leu Ser Ser
    50                  55                  60

Ser Arg Tyr His Asp Gln Ala Val Leu Phe
65                  70

<210> SEQ ID NO 3
<211> LENGTH: 74
<212> TYPE: PRT
<213> ORGANISM: Homo sapiens

<400> SEQUENCE: 3

Met Ser Pro Ser Pro Thr Ala Leu Phe Cys Leu Gly Leu Cys Pro Gly
 1               5                  10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr His Asp Gln Ala Val Leu Phe
65                  70

<210> SEQ ID NO 4
<211> LENGTH: 1681
<212> TYPE: DNA
<213> ORGANISM: Homo sapiens

<400> SEQUENCE: 4
acagggctga ggaaccatgt ctccatcccc gaccgccctc ttctgtcttg ggctgtgtct     60
ggggcgtgtg ccagcgcaga gtggaccgct ccccaagccc tccctccagg ctctgcccag    120
ctccctggtg cccctggaga agccagtgac cctccggtgc cagggacctc cgggcgtgga    180
cctgtaccgc ctggagaagc tgagttccag caggtaccag gatcaggcag tcctcttcat    240
cccggccatg aagagaagtc tggctggacg ctaccgctgc tcctaccaga acggaagcct    300
ctggtccctg cccaacgacc agctggagct cgttgccacg ggagtttttg ccaaaccctc    360
gctctcagcc cagcccggcc cggcggtgtc gtcaggaggg gacgtaaccc tacagtgtca    420
gactcggtat ggcttttgacc aatttgctct gtacaaggaa ggggaccctg cgccctacaa    480
gaatcccgag agatggtacc gggctagttt ccccatcatc acggtgaccg ccgcccacag    540
cggaacctac cgatgctaca gcttctccag caggacccca tacctgtggt cggccccag     600 cgacccctg gagcttgtgg tcacaggaac ctctgtgacc ccagccggt taccaacaga    660 accaccttcc tcggtagcag aattctcaga agccaccgct gaactgaccg tctcattcac    720
aaacaaagtc ttcacaactg agacttctag gagtatcacc accagtccaa aggagtcaga    780
ctctccagct ggtcctgccc gccagtacta ccaagggc aacctggtcc ggatatgcct    840
cggggctgtg atcctaataa tcctggcggg gtttctggca gaggactggc acagccggag    900
gaagcgcctg cggcacaggg gcagggctgt gcagaggccg cttccgcccc tgccgccct    960 cccgcagacc cggaaatcac acgggggtca ggatggaggc cgacaggatg ttcacagccg   1020
cgggttatgt tcatgaccgc tgaacccag gcacggtcgt atccaaggga gggatcatgg   1080
catgggaggc gactcaaaga ctggcgtgtg tggagcgtgg aagcaggagg cagaggcta   1140 cagctgtgga aacagaggcca tgctgcctcc tcctggtgtt ccatcaggga tccgtcggcc   1200
agtgtctgtc tgtctgtctg cctctctgtc tgagggcacc ctccatttgg gatggaagga   1260

```
atctgtggag accccatcct cctccctgca cactgtggat gacatggtac cctggctgga    1320
ccacatactg gcctctttct tcaacctctc taatatgggc tccagacgga tctctaaggt    1380
tcccagctct cagggttgac tctgttccat cctctgtgca aaatcctcct gtgcttccct    1440
ttggccctct gtgctcttgt ctggttttcc ccagaaactc tcaccctcac tccatctccc    1500
actgcagtct aacaaatctc ctttcgtctc tcagaacggg tcttgcaggc agtttgggta    1560
tgtcattcat tttccttagt gtaaaactag cacgttgccc gcttcccttc acattagaaa    1620
acaagatcag cctgtgcaac atggtgaaac ctcatctcta ccaacaaaaa aaaaaaaaa     1680 a                                                                    1681
```

<210> SEQ ID NO 5
<211> LENGTH: 339
<212> TYPE: PRT
<213> ORGANISM: Homo sapiens

<400> SEQUENCE: 5

```
Met Ser Pro Ser Pro Thr Ala Leu Phe Cys Leu Gly Leu Cys Leu Gly
  1               5                  10                  15

Arg Val Pro Ala Gln Ser Gly Pro Leu Pro Lys Pro Ser Leu Gln Ala
                 20                  25                  30

Leu Pro Ser Ser Leu Val Pro Leu Glu Lys Pro Val Thr Leu Arg Cys
             35                  40                  45

Gln Gly Pro Pro Gly Val Asp Leu Tyr Arg Leu Glu Lys Leu Ser Ser
         50                  55                  60

Ser Arg Tyr Gln Asp Gln Ala Val Leu Glu Ile Pro Ala Met Lys Arg
 65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
            100                 105                 110

Lys Asx Ser Leu Ser Ala Gln Pro Gly Pro Ala Val Ser Ser Gly Gly
            115                 120                 125

Asp Val Thr Leu Gln Cys Gln Thr Arg Tyr Gly Phe Asp Gln Phe Ala
        130                 135                 140

Leu Tyr Lys Glu Gly Asp Pro Ala Pro Tyr Lys Asn Pro Glu Arg Trp
145                 150                 155                 160

Tyr Arg Ala Ser Phe Asx Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285
```

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
gagctcagga cagggctgag gaacc                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 7
gtgccctcat gagtcgcctc ccatg                                          25

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
ataggcccag ccggcctcag agtggaccgc                                     30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
tgttctagac cgttgccctt ggtgtagtac                                     30

<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (3)
<223> OTHER INFORMATION: L or T
<220> FEATURE:
<221> NAME/KEY: MOD_RES
<222> LOCATION: (4)
<223> OTHER INFORMATION: A or L
<220> FEATURE:
<221> NAME/KEY: MOD_RES
<222> LOCATION: (7)

```
<223> OTHER INFORMATION: Y or Q
<220> FEATURE:
<221> NAME/KEY: MOD_RES
<222> LOCATION: (10)
<223> OTHER INFORMATION: S or P
<220> FEATURE:
<221> NAME/KEY: MOD_RES
<222> LOCATION: (12)
<223> OTHER INFORMATION: Q or V
<220> FEATURE:
<221> NAME/KEY: MOD_RES
<222> LOCATION: (15)
<223> OTHER INFORMATION: L or any amino acid

<400> SEQUENCE: 10

Xaa Val Xaa Xaa Arg Arg Xaa Arg Pro Xaa Tyr Xaa Asp Leu Xaa
 1               5                  10                  15

<210> SEQ ID NO 11
<211> LENGTH: 10
<212> TYPE: PRT
<213> ORGANISM: Homo sapiens
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (2)
<223> OTHER INFORMATION: F or V
<220> FEATURE:
<221> NAME/KEY: MOD_RES
<222> LOCATION: (3)
<223> OTHER INFORMATION: T or L
<220> FEATURE:
<221> NAME/KEY: MOD_RES
<222> LOCATION: (10)
<223> OTHER INFORMATION: Any amino acid

<400> SEQUENCE: 11

Xaa Xaa Xaa Ala Gly Arg Tyr Gly Pro Xaa
 1               5                  10

<210> SEQ ID NO 12
<211> LENGTH: 17
<212> TYPE: PRT
<213> ORGANISM: Homo sapiens
<220> FEATURE:
<221> NAME/KEY: MOD_RES
<222> LOCATION: (1)
<223> OTHER INFORMATION: P or L
<220> FEATURE:
<221> NAME/KEY: MOD_RES
<222> LOCATION: (2)
<223> OTHER INFORMATION: S or R
<220> FEATURE:
<221> NAME/KEY: MOD_RES
<222> LOCATION: (3)
<223> OTHER INFORMATION: L or E
<220> FEATURE:
<221> NAME/KEY: MOD_RES
<222> LOCATION: (4)
<223> OTHER INFORMATION: Q, Y or F
<220> FEATURE:
<221> NAME/KEY: MOD_RES
<222> LOCATION: (5)
<223> OTHER INFORMATION: A or R
<220> FEATURE:
<221> NAME/KEY: MOD_RES
<222> LOCATION: (6)
<223> OTHER INFORMATION: L or Y
<220> FEATURE:
<221> NAME/KEY: MOD_RES
<222> LOCATION: (7)
<223> OTHER INFORMATION: P or Q
```

```
<220> FEATURE:
<221> NAME/KEY: MOD_RES
<222> LOCATION: (8)
<223> OTHER INFORMATION: S or N
<220> FEATURE:
<221> NAME/KEY: MOD_RES
<222> LOCATION: (9)
<223> OTHER INFORMATION: S or Q
<220> FEATURE:
<221> NAME/KEY: MOD_RES
<222> LOCATION: (10)
<223> OTHER INFORMATION: L or A
<220> FEATURE:
<221> NAME/KEY: MOD_RES
<222> LOCATION: (11)
<223> OTHER INFORMATION: V or I
<220> FEATURE:
<221> NAME/KEY: MOD_RES
<222> LOCATION: (14)
<223> OTHER INFORMATION: I, Y or E
<220> FEATURE:
<221> NAME/KEY: MOD_RES
<222> LOCATION: (16)
<223> OTHER INFORMATION: A or R
<220> FEATURE:
<221> NAME/KEY: MOD_RES
<222> LOCATION: (17)
<223> OTHER INFORMATION: Any amino acid

<400> SEQUENCE: 12

Xaa Xaa Xaa Xaa Xaa Xaa Xaa Xaa Xaa Xaa Xaa Pro Phe Xaa Thr Xaa
 1               5                  10                  15

Xaa

<210> SEQ ID NO 13
<211> LENGTH: 20
<212> TYPE: PRT
<213> ORGANISM: Homo sapiens
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (18)
<223> OTHER INFORMATION: Any amino acid

<400> SEQUENCE: 13

Lys Xaa Val Leu Ala Arg Arg Tyr Arg Pro Pro Tyr Gln Asp Leu Tyr
 1               5                  10                  15

Arg Xaa Glu Lys
         20

<210> SEQ ID NO 14
<211> LENGTH: 19
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Any amino acid

<400> SEQUENCE: 14

Lys Leu Asp Xaa Xaa Arg Tyr Gln Asp Gln Ala Val Leu Phe Ile Pro
 1               5                  10                  15

Ala Met Lys

<210> SEQ ID NO 15
<211> LENGTH: 13
<212> TYPE: PRT
```

```
<213> ORGANISM: Homo sapiens
<220> FEATURE:
<221> NAME/KEY: MOD_RES
<222> LOCATION: (1)
<223> OTHER INFORMATION: T or any amino acid
<220> FEATURE:
<221> NAME/KEY: MOD_RES
<222> LOCATION: (2)
<223> OTHER INFORMATION: L, A or V
<220> FEATURE:
<221> NAME/KEY: MOD_RES
<222> LOCATION: (3)
<223> OTHER INFORMATION: M or H
<220> FEATURE:
<221> NAME/KEY: MOD_RES
<222> LOCATION: (4)
<223> OTHER INFORMATION: E or L
<220> FEATURE:
<221> NAME/KEY: MOD_RES
<222> LOCATION: (5)
<223> OTHER INFORMATION: N or R
<220> FEATURE:
<221> NAME/KEY: MOD_RES
<222> LOCATION: (6)
<223> OTHER INFORMATION: F or Q
<220> FEATURE:
<221> NAME/KEY: MOD_RES
<222> LOCATION: (7)
<223> OTHER INFORMATION: T or V
<220> FEATURE:
<221> NAME/KEY: MOD_RES
<222> LOCATION: (8)
<223> OTHER INFORMATION: A or Y
<220> FEATURE:
<221> NAME/KEY: MOD_RES
<222> LOCATION: (9)
<223> OTHER INFORMATION: F, E, G or any amino acid
<220> FEATURE:
<221> NAME/KEY: MOD_RES
<222> LOCATION: (10)
<223> OTHER INFORMATION: V or L
<220> FEATURE:
<221> NAME/KEY: MOD_RES
<222> LOCATION: (11)
<223> OTHER INFORMATION: D or M
<220> FEATURE:
<221> NAME/KEY: MOD_RES
<222> LOCATION: (12)
<223> OTHER INFORMATION: A or any amino acid
<220> FEATURE:
<221> NAME/KEY: MOD_RES
<222> LOCATION: (13)
<223> OTHER INFORMATION: Any amino acid

<400> SEQUENCE: 15

Xaa Xaa Xaa Xaa Xaa Xaa Xaa Xaa Xaa Xaa Xaa Xaa Xaa
 1               5                  10

<210> SEQ ID NO 16
<211> LENGTH: 7
<212> TYPE: PRT
<213> ORGANISM: Homo sapiens

<400> SEQUENCE: 16

Leu Val Asn Glu Leu Thr Phe
 1               5

<210> SEQ ID NO 17
<211> LENGTH: 18
<212> TYPE: PRT
<213> ORGANISM: Homo sapiens
<220> FEATURE:
<221> NAME/KEY: MOD_RES
<222> LOCATION: (17)..(18)
<223> OTHER INFORMATION: Any amino acid
```

```
<400> SEQUENCE: 17

Asp Ala Ile Pro Glu Asn Leu Pro Pro Leu Thr Ala Asp Phe Ala Glu
 1               5                  10                  15

Xaa Xaa

<210> SEQ ID NO 18
<211> LENGTH: 16
<212> TYPE: PRT
<213> ORGANISM: Homo sapiens

<400> SEQUENCE: 18

Lys Pro Ser Leu Gln Ala Leu Pro Ser Ser Leu Val Pro Leu Glu Lys
 1               5                  10                  15

<210> SEQ ID NO 19
<211> LENGTH: 18
<212> TYPE: PRT
<213> ORGANISM: Homo sapiens
<220> FEATURE:
<221> NAME/KEY: MOD_RES
<222> LOCATION: (18)
<223> OTHER INFORMATION: Any amino acid

<400> SEQUENCE: 19

Lys Pro Ser Leu Gln Ala Leu Pro Ser Ser Leu Val Pro Phe Ile Thr
 1               5                  10                  15

Ala Xaa

<210> SEQ ID NO 20
<211> LENGTH: 19
<212> TYPE: PRT
<213> ORGANISM: Homo sapiens

<400> SEQUENCE: 20

Lys Leu Ser Ser Ser Arg Tyr Gln Asp Gln Ala Val Leu Phe Ile Pro
 1               5                  10                  15

Met Ala Lys

<210> SEQ ID NO 21
<211> LENGTH: 19
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: Any amino acid

<400> SEQUENCE: 21

Lys Leu Asp Xaa Xaa Arg Tyr Gln Asp Gln Ala Val Leu Phe Ile Pro
 1               5                  10                  15

Met Ala Lys

<210> SEQ ID NO 22
<211> LENGTH: 16
<212> TYPE: PRT
<213> ORGANISM: Homo sapiens
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (11)
<223> OTHER INFORMATION: S or P
```

```
<400> SEQUENCE: 22

Lys Xaa Val Leu Ala Arg Arg Tyr Arg Pro Xaa Tyr Gln Asp Leu Leu
  1               5                  10                  15

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(25)
<223> OTHER INFORMATION: A, T, C or G

<400> SEQUENCE: 23
gnmgntaymg nccnhsntay carga                                          25

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(22)
<223> OTHER INFORMATION: A, T, C or G

<400> SEQUENCE: 24
gntaymgncc nhsntaycar ga                                             22

<210> SEQ ID NO 25
<211> LENGTH: 11
<212> TYPE: PRT
<213> ORGANISM: Homo sapiens
<220> FEATURE:
<221> NAME/KEY: MOD_RES
<222> LOCATION: (1)..(11)
<223> OTHER INFORMATION: Any amino acid

<400> SEQUENCE: 25

Lys Xaa Phe Thr Ala Gly Arg Tyr Gly Pro Xaa
  1               5                  10

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(23)
<223> OTHER INFORMATION: A, T, C or G

<400> SEQUENCE: 26
ttyacngcng gnmgntaygg ncc                                            23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(21)
```

<223> OTHER INFORMATION: A, T, C or G

<400> SEQUENCE: 27
ytnttyathc cngcnatgaa r                                      21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(21)
<223> OTHER INFORMATION: A, T C or G

<400> SEQUENCE: 28
narnacngcy tgrtcytgrt a                                      21

<210> SEQ ID NO 29
<211> LENGTH: 6
<212> TYPE: PRT
<213> ORGANISM: Homo sapiens

<400> SEQUENCE: 29

Ser Ser Ser Arg Tyr Gln
 1               5

<210> SEQ ID NO 30
<211> LENGTH: 6
<212> TYPE: PRT
<213> ORGANISM: Homo sapiens

<400> SEQUENCE: 30

Ser Ser Ser Arg Tyr His
 1               5

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 31
cccaccatgt ctccatcccc gac                                    23

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 32
gtaatacgac tcactatagg gc                                     22

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
cgacgatacc gcccc                                                       15

<210> SEQ ID NO 34
<211> LENGTH: 4
<212> TYPE: PRT
<213> ORGANISM: Homo sapiens

<400> SEQUENCE: 34

Asp Asp Asp Lys
 1

<210> SEQ ID NO 35
<211> LENGTH: 17
<212> TYPE: PRT
<213> ORGANISM: Homo sapiens
<220> FEATURE:
<221> NAME/KEY: MOD_RES
<222> LOCATION: (17)
<223> OTHER INFORMATION: Any amino acid

<400> SEQUENCE: 35

Pro Ser Leu Gln Ala Leu Pro Ser Ser Leu Val Pro Phe Ile Thr Ala
 1               5                  10                  15

Xaa

<210> SEQ ID NO 36
<211> LENGTH: 1200
<212> TYPE: DNA
<213> ORGANISM: Homo sapiens
<220> FEATURE:
<221> NAME/KEY: CDS
<222> LOCATION: (41)..(1147)

<400> SEQUENCE: 36
caacttgaga agatcaaaaa acaactaatt attcgaaacg atg aga ttt cct tca         55
                                             Met Arg Phe Pro Ser
                                              1               5 att ttt act gct gtt tta ttc gca gca tcc tcc gca tta gct gct cca       103
Ile Phe Thr Ala Val Leu Phe Ala Ala Ser Ser Ala Leu Ala Ala Pro
             10                  15                  20 gtc aac act aca aca gaa gat gaa acg gca caa att ccg gct gaa gct       151
Val Asn Thr Thr Thr Glu Asp Glu Thr Ala Gln Ile Pro Ala Glu Ala
         25                  30                  35 gtc atc ggt tac tca gat tta gaa ggg gat ttc gat gtt gct gtt ttg       199
Val Ile Gly Tyr Ser Asp Leu Glu Gly Asp Phe Asp Val Ala Val Leu
     40                  45                  50 cca ttt tcc aac agc aca aat aac ggg tta ttg ttt ata aat act act       247
Pro Phe Ser Asn Ser Thr Asn Asn Gly Leu Leu Phe Ile Asn Thr Thr
 55                  60                  65 att gcc agc att gct gct aaa gaa gaa ggg gta tct ctc gag aaa aga       295
Ile Ala Ser Ile Ala Ala Lys Glu Glu Gly Val Ser Leu Glu Lys Arg
 70                  75                  80                  85 gag gct gaa gct gaa ttc acg tgg ccc agc cgg cct cag agt gga ccg       343
Glu Ala Glu Ala Glu Phe Thr Trp Pro Ser Arg Pro Gln Ser Gly Pro
                 90                  95                 100 ctc ccc aag ccc tcc ctc cag gct ctg ccc agc tcc ctg gtg ccc ctg       391
Leu Pro Lys Pro Ser Leu Gln Ala Leu Pro Ser Ser Leu Val Pro Leu
            105                 110                 115 gag aag cca gtg acc ctc cgg tgc cag gga cct ccg ggc gtg gac ctg       439
Glu Lys Pro Val Thr Leu Arg Cys Gln Gly Pro Pro Gly Val Asp Leu
        120                 125                 130 tac cgc ctg gag aag ctg agt tcc agc agg tac cag gat cag gca gtc       487
Tyr Arg Leu Glu Lys Leu Ser Ser Ser Arg Tyr Gln Asp Gln Ala Val

```
        135                 140                 145
ctc ttc atc ccg gcc atg aag aga agt ctg gct gga cgc tac cgc tgc      535
Leu Phe Ile Pro Ala Met Lys Arg Ser Leu Ala Gly Arg Tyr Arg Cys
150                 155                 160                 165 tcc tac cag aac gga agc ctc tgg tcc ctg ccc agc gac cag ctg gag      583
Ser Tyr Gln Asn Gly Ser Leu Trp Ser Leu Pro Ser Asp Gln Leu Glu
                170                 175                 180 ctc gtt gcc acg gga gtt ttt gcc aaa ccc tcg ctc tca gcc cag ccc      631
Leu Val Ala Thr Gly Val Phe Ala Lys Pro Ser Leu Ser Ala Gln Pro
                185                 190                 195 ggc ccg gcg gtg tcg tca gga ggg gac gta acc cta cag tgt cag act      679
Gly Pro Ala Val Ser Ser Gly Gly Asp Val Thr Leu Gln Cys Gln Thr
            200                 205                 210 cgg tat ggc ttt gac caa ttt gct ctg tac aag gaa ggg gac cct gcg      727
Arg Tyr Gly Phe Asp Gln Phe Ala Leu Tyr Lys Glu Gly Asp Pro Ala
        215                 220                 225 ccc tac aag aat ccc gag aga tgg tac cgg gct agt ttc ccc atc atc      775
Pro Tyr Lys Asn Pro Glu Arg Trp Tyr Arg Ala Ser Phe Pro Ile Ile
230                 235                 240                 245 acg gtg acc gcc gcc cac agc gga acc tac cga tgc tac agc ttc tcc      823
Thr Val Thr Ala Ala His Ser Gly Thr Tyr Arg Cys Tyr Ser Phe Ser
                250                 255                 260 agc agg gac cca tac ctg tgg tcg gcc ccc agc gac ccc ctg gag ctt      871
Ser Arg Asp Pro Tyr Leu Trp Ser Ala Pro Ser Asp Pro Leu Glu Leu
                265                 270                 275 gtg gtc aca gga acc tct gtg acc ccc agc cgg tta cca aca gaa cca      919
Val Val Thr Gly Thr Ser Val Thr Pro Ser Arg Leu Pro Thr Glu Pro
            280                 285                 290 cct tcc tcg gta gca gaa ttc tca gaa gcc acc gct gaa ctg acc gtc      967
Pro Ser Ser Val Ala Glu Phe Ser Glu Ala Thr Ala Glu Leu Thr Val
        295                 300                 305 tca ttc aca aac aaa gtc ttc aca act gag act tct agg agt atc acc     1015
Ser Phe Thr Asn Lys Val Phe Thr Thr Glu Thr Ser Arg Ser Ile Thr
310                 315                 320                 325 acc agt cca aag gag tca gac tct cca gct ggt cct gcc cgc cag tac     1063
Thr Ser Pro Lys Glu Ser Asp Ser Pro Ala Gly Pro Ala Arg Gln Tyr
                330                 335                 340 tac acc aag ggc aac ggt cta gaa caa aaa ctc atc tca gaa gag gat     1111
Tyr Thr Lys Gly Asn Gly Leu Glu Gln Lys Leu Ile Ser Glu Glu Asp
                345                 350                 355 ctg aat agc gcc gtc gac cat cat cat cat cat cat tgagtttgta         1157
Leu Asn Ser Ala Val Asp His His His His His His
                360                 365 gccttagaca tgactgttcc tcagttcaag ttgggcactt acg                     1200

<210> SEQ ID NO 37
<211> LENGTH: 369
<212> TYPE: PRT
<213> ORGANISM: Homo sapiens

<400> SEQUENCE: 37

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60
```

-continued

```
Phe Ile Asn Thr Thr Ile Ala Ser Ile Ala Ala Lys Glu Glu Gly Val
 65                  70                  75                  80

Ser Leu Glu Lys Arg Glu Ala Glu Ala Glu Phe Thr Trp Pro Ser Arg
                 85                  90                  95

Pro Gln Ser Gly Pro Leu Pro Lys Pro Ser Leu Gln Ala Leu Pro Ser
                100                 105                 110

Ser Leu Val Pro Leu Glu Lys Pro Val Thr Leu Arg Cys Gln Gly Pro
                115                 120                 125

Pro Gly Val Asp Leu Tyr Arg Leu Glu Lys Leu Ser Ser Ser Arg Tyr
            130                 135                 140

Gln Asp Gln Ala Val Leu Phe Ile Pro Ala Met Lys Arg Ser Leu Ala
145                 150                 155                 160

Gly Arg Tyr Arg Cys Ser Tyr Gln Asn Gly Ser Leu Trp Ser Leu Pro
                165                 170                 175

Ser Asp Gln Leu Glu Leu Val Ala Thr Gly Val Phe Ala Lys Pro Ser
                180                 185                 190

Leu Ser Ala Gln Pro Gly Pro Ala Val Ser Ser Gly Gly Asp Val Thr
            195                 200                 205

Leu Gln Cys Gln Thr Arg Tyr Gly Phe Asp Gln Phe Ala Leu Tyr Lys
    210                 215                 220

Glu Gly Asp Pro Ala Pro Tyr Lys Asn Pro Glu Arg Trp Tyr Arg Ala
225                 230                 235                 240

Ser Phe Pro Ile Ile Thr Val Thr Ala Ala His Ser Gly Thr Tyr Arg
                245                 250                 255

Cys Tyr Ser Phe Ser Ser Arg Asp Pro Tyr Leu Trp Ser Ala Pro Ser
                260                 265                 270

Asp Pro Leu Glu Leu Val Val Thr Gly Thr Ser Val Thr Pro Ser Arg
            275                 280                 285

Leu Pro Thr Glu Pro Pro Ser Ser Val Ala Glu Phe Ser Glu Ala Thr
    290                 295                 300

Ala Glu Leu Thr Val Ser Phe Thr Asn Lys Val Phe Thr Thr Glu Thr
305                 310                 315                 320

Ser Arg Ser Ile Thr Thr Ser Pro Lys Glu Ser Asp Ser Pro Ala Gly
                325                 330                 335

Pro Ala Arg Gln Tyr Tyr Thr Lys Gly Asn Gly Leu Glu Gln Lys Leu
            340                 345                 350

Ile Ser Glu Glu Asp Leu Asn Ser Ala Val Asp His His His His
    355                 360                 365

His
```